(12) United States Patent
Gabella et al.

(10) Patent No.: US 12,408,882 B2
(45) Date of Patent: Sep. 9, 2025

(54) MEDICAL IMAGING APPARATUS HAVING A RADIATION SOURCE AND AN IMAGING DEVICE WITH ROTATIONAL ARMS

(71) Applicant: PRISTEM SA, Lausanne (CH)

(72) Inventors: Thomas Gabella, Lausanne (CH); Nicolas Ganshof Van Der Meersch, Vufflens-le-Château (CH); Hubert Blanchard, St-Saphorin (CH)

(73) Assignee: PRISTEM SA, Lausanne (CH)

( * ) Notice: Subject to any disclaimer, the term of this patent is extended or adjusted under 35 U.S.C. 154(b) by 131 days.

(21) Appl. No.: 18/011,498

(22) PCT Filed: Jun. 29, 2021

(86) PCT No.: PCT/IB2021/055812
§ 371 (c)(1),
(2) Date: Dec. 19, 2022

(87) PCT Pub. No.: WO2022/003561
PCT Pub. Date: Jan. 6, 2022

(65) Prior Publication Data
US 2023/0255579 A1    Aug. 17, 2023

(30) Foreign Application Priority Data
Jun. 29, 2020  (EP) .................................. 20182896

(51) Int. Cl.
*A61B 6/00* (2024.01)
*A61B 6/10* (2006.01)

(52) U.S. Cl.
CPC ............ *A61B 6/4435* (2013.01); *A61B 6/105* (2013.01); *A61B 6/4452* (2013.01); *A61B 6/447* (2013.01); *A61B 6/4476* (2013.01); *A61B 6/54* (2013.01)

(58) Field of Classification Search
None
See application file for complete search history.

(56) References Cited

U.S. PATENT DOCUMENTS

| 3,784,837 A | 1/1974 | Holmström |
| 3,892,967 A | 7/1975 | Grady et al. |
| 4,756,016 A * | 7/1988 | Grady ................. A61B 6/4441 378/197 |

(Continued)

FOREIGN PATENT DOCUMENTS

DE    102010041201 A1    3/2012

OTHER PUBLICATIONS

International Search Report for PCT/IB2021/055812, mailed Jan. 4, 2022, 6 pages.

(Continued)

*Primary Examiner* — Hoon K Song
(74) *Attorney, Agent, or Firm* — Nixon & Vanderhye P.C.

(57) ABSTRACT

A radiation apparatus including a support column, a rotatable arm that is configured to rotate around a first pivot relative to the support column, a first arm rotatably attached to one side of the rotatable arm to rotate about a second pivot, the first arm holding a imaging device, and a second arm rotatably attached to an other side of the rotatable arm to rotate about a third pivot, the second arm holding a radiation source, wherein radiation axis of the radiation source is configured to irradiate an imaging plane of the imaging device.

22 Claims, 21 Drawing Sheets

(56) References Cited

U.S. PATENT DOCUMENTS

| | | | |
|---|---|---|---|
| 7,519,441 | B2 | 4/2009 | Boomgaarden |
| 9,001,969 | B2 | 4/2015 | Murakoshi et al. |
| 9,274,014 | B2 | 3/2016 | Janik et al. |
| 9,298,194 | B2 | 3/2016 | Lee et al. |
| 2005/0094770 | A1 | 5/2005 | Fadler et al. |
| 2010/0008474 | A1 | 1/2010 | Hornung et al. |
| 2010/0303207 | A1* | 12/2010 | Tsujii .................. A61B 6/4405 378/197 |
| 2015/0055760 | A1* | 2/2015 | Barker ................ A61B 6/4476 378/197 |
| 2018/0070901 | A1 | 3/2018 | Gabella et al. |
| 2018/0271461 | A1* | 9/2018 | Simmons ............ A61B 6/4405 |
| 2021/0137474 | A1* | 5/2021 | Mungase ............ A61B 6/4405 |

OTHER PUBLICATIONS

Written Opinion of the ISA for PCT/IB2021/055812, mailed Jan. 4, 2022, 11 pages.
European Search Report dated Mar. 15, 2021, issued in European Application No. 20182896.9, 5 pages.
Written Opinion dated Mar. 15, 2021, issued in European Application No. 20182896.9, 5 pages.

* cited by examiner

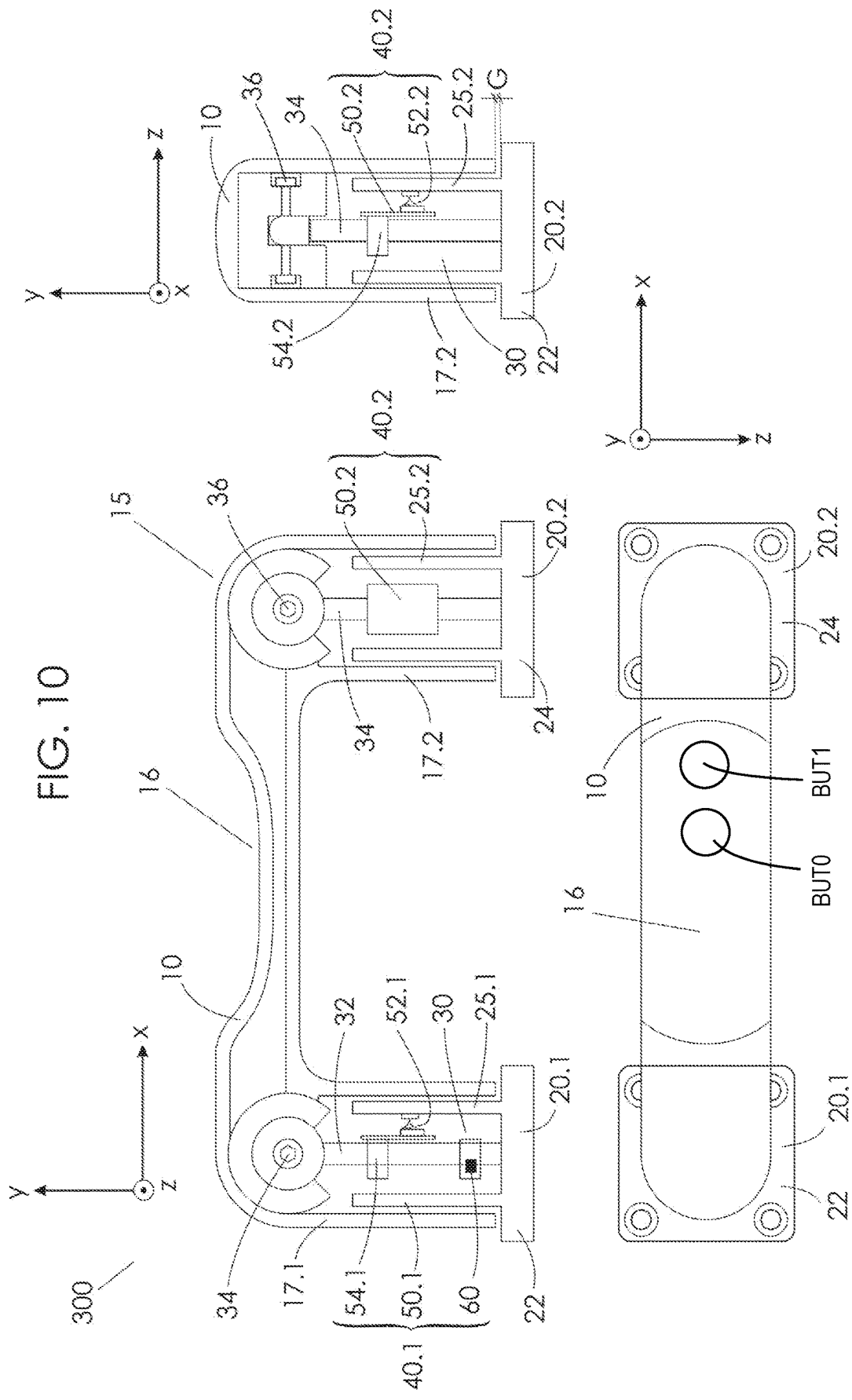

MEDICAL IMAGING APPARATUS HAVING A RADIATION SOURCE AND AN IMAGING DEVICE WITH ROTATIONAL ARMS

CROSS-REFERENCE TO RELATED APPLICATIONS

This application is the U.S. national phase of International Application No. PCT/IB2021/055812 filed Jun. 29, 2021, which designated the U.S. and claims priority to European Patent Application No. 20182896.9 that was filed on Jun. 29, 2020, the entire contents of each of which are hereby incorporated by reference.

FIELD OF THE INVENTION

The present invention described herein relates to radiography appliances, particularly medical imaging apparatuses having a radiation source and an imaging device, for example an X-ray source and imaging device. It relates more specifically to radiography appliances in which the radiation source and the detector are positioned at opposing ends of a mobile arm.

BACKGROUND

In the context of the present application, reference is made to an already existing radiography appliance or apparatus 1, more specifically an X-ray appliance, and the description of arm 5 that is mounted relative to a column 3. The radiography appliance was described in U.S. Patent Publication Number 2018/0070901, this reference herewith incorporated by reference in its entirety. FIG. 1 illustrates the radiography appliance (or a medical imaging appliance) 1 on which the present application is based. The appliance 1 comprises a support column 3, an arm 5 mounted with the ability to move and articulated on the column 3. The arm 5 being able to slide along the column 3 and to rotate about an axis oriented perpendicular to the direction of the column 3. The arm 5 further comprises a first support device DS1 able to bear a radiation source 7 on a first side of the arm and a second support device DS2 able to bear a detector 9 on a second side of the arm. The first or the second support device are able to move and can move along the arm 5. As shown in FIGS. 3A to 3C, radiography system 1 additionally comprises anti-rotation means 11 configured to limit or prevent the rotation of the arm 5 with respect to the support column 3 so as to avoid collision between the arm and the ground and therefore avoid damage to the radiography appliance 1.

However, many of the state of the art radiation devices and systems rely on linear motion devices and motorization for moving either X-ray source, X-ray imaging device, or both, to change the source-imaging distance SID. For example, as shown in U.S. Pat. No. 9,001,969, this reference herewith incorporated by reference in its entirety, many X-ray systems rely on linear motion devices to change a source-imaging distance SID, for example as shown in FIG. 17, where the X-ray source 11 is slidably attached to a groove 73, and the X-ray source 11 and the imaging unit 12 oppose each other. Moving the X-ray source 11 along the first groove 73 adjusts a distance between the X-ray focal point 18 b and the detection surface of the FPD 30.

U.S. Pat. No. 3,784,837 is directed to an X-ray device including an X-ray tube 1 and an X-ray image amplifier 2 which are hung by a stand 3 from ceiling 4. The stand consists of a column 5, a bracket 7 swingable upon the column about a horizontal axle 6, a carrying arm 9 for the X-ray tube 1, carrying arm 9 being mounted upon one end of the bracket 7 and being swingable about a horizontal axle 8 extending parallel to the axle 6, and a carrying arm 11 for the X-ray image amplifier 2 which is located at the other end of the bracket 7 and is swingable about a horizontal axle 10 also extending parallel to the axle 6. However, this X-ray device does not have any mechanism or other arrangement to vary a distance between X-ray tube 1 and X-ray image amplifier 2 at different positions.

In addition, In the field of X-ray and other medical imaging apparatuses, different solutions have been proposed that allow to assist a movement or displacement of an element of the imaging apparatus by motor support. For example, U.S. Pat. No. 7,519,441 discusses a method for determining a kinetic assistance that a manually-propelled movement of the medical imaging positioning apparatus, and a step of determining at least one direction from a pre-stored table of forces and positions. As an implementation a moving and stationary member that move along a linear axis is shown. Also, as another example, U.S. Pat. No. 9,298,194 discusses a method where when operator moves a handle in a direction and with a magnitude of force to position the imaging unit to a higher position, imaging unit moves upward in a direction and with a magnitude of force, for example by increasing drive power of a motor provided on each axis of the medical equipment taking into consideration the direction and magnitude of force applied to the handle. Also, U.S. Pat. No. 9,274,014 describes a handle that can be used for measuring torques and forces that can be attached to robot surgical system.

Accordingly, despite all the advancements in the background art of radiation devices and systems, in particular X-ray systems, strongly improved radiation systems and devices are desired, to increase their lifetime, improve sealing and encapsulation of components, reduce manufacturing and operational costs, to provide for more rugged and solid solutions, and to reduce the number of electrical components needed, to provide for a simplified mechanical operation requiring less active parts. For example, improved radiation systems and devices are desired, to minimize maintenance costs and increase durability, and also to operate them in challenging environmental conditions.

Also, with respect to assisted and motorized radiation devices, advanced and more specific solutions are desired, specific to X-ray, radiography, and other medical imaging devices, for the measurement, calculation and application of different types of assistive torques and forces to a medical imaging device or system.

SUMMARY

According to one aspect of the present invention, a radiation imaging apparatus is provided. Preferably, the radiation imaging apparatus includes a main rotatable arm that is configured to rotate around a first pivot relative to a device for pivotably holding the main rotatable arm, a first arm rotatably attached to one side of the main rotatable arm to rotate about a second pivot, the first arm holding a imaging device, a second arm rotatably attached to an other side of the main rotatable arm to rotate about a third pivot, the second arm holding a radiation source, a radiation axis of the radiation source is configured to irradiate an imaging plane of the imaging device, a linking means that links a rotation of the first arm to the rotation of the second arm such that a rotation of the first arm causes a rotation of the second arm and vice versa in opposite rotational directions for adjusting a source image-receptor distance SID.

Moreover, according to another aspect of the present invention, a radiation imaging apparatus is provided, preferably including a linking means includes a linking mechanism having a transversal bar rotatably attached to the first arm at a pivot point and rotatably attached to the second arm to a pivot point, the transversal bar mechanically linking a rotation of the first arm with a rotation of the second arm for causing the opposite rotational directions for adjusting the source image-receptor distance SID.

According to still another aspect of the present invention, a linear guiding structure for a support column of a radiation apparatus or system is provided, to provide for a linear sliding mechanism to a radiation arm. The radiation arm configured to slide along a vertical opening of the support column, and the linear guiding structure preferably includes a first guiding rail, a second guiding rail arranged in parallel to the first guiding rail, a first wheel in contact with the first guiding rail, and a second wheel in contact with the second guiding rail, arranged at a distance from the first wheel. Moreover, the first guiding rail is arranged parallel to a longitudinal extension of the support column, the first guiding rail arranged to be closer to the vertical opening as compared to the second guiding rail, and wherein the radiation arm is attached to the linear guiding structure such that the first wheel is urged agains the first guiding rail, and the second wheel is urged against the second guiding rail by a torque caused by a weight of the radiation arm.

Moreover, according to yet another aspect of the present invention, a handle for motor-assisted moving an arm of a radiation apparatus is provided. Preferably, the handle includes a holding element configured to be held by a hand of a user to move the arm of the radiation apparatus, a base member configured to attached to the arm, an interconnection member interconnecting the holding element and the base member, a portion of the interconnection element configured to bend or displace upon engagement of the user with the holding element, and a measurement unit configured to measure a value indicative of a force or a torque applied by the user to the handle and a value indicative of an orientation of the handle.

According to still another aspect of the present invention, a height-adjustable foot for a radiation device is provided, the foot preferably installable at a bottom wall or base of a support column. Preferably, the height-adjustable foot includes a traversing bolt (530) having an exterior threading, a holding element having a through-hole with an interior threading, the exterior threading of the traversing bolt configured to threadably engage with the interior threading; and a foot element arranged at a distal portion of the traversing bolt wherein a distance of the foot element relative to the holding element can be varied by a rotation of traversing bolt relative to holding element.

According to yet another aspect of the present invention, a radiation imaging apparatus is provided. Preferably, the radiation apparatus includes a support column, a rotatable arm that is configured to rotate around a first pivot relative to the support column for pivotably holding the rotatable arm, and is configured to be linearly moved up and down along an axis of the support column, the rotatable arm configured to hold a radiation imaging device and a radiation source, a motor configured to assist a linear motion of the rotatable arm along the axis of the support column, and a handle configured to measure an effort by user to move rotatable arm up and down along an axis of the support column.

Herein, identical reference numerals are used, where possible, to designate identical elements that are common to the figures. Also, the images in the drawings are simplified for illustration purposes and may not be depicted to scale.

BRIEF DESCRIPTION OF THE SEVERAL VIEWS OF THE DRAWINGS

Further features and advantages of the present invention will become more clearly apparent from reading the detailed description which stems from one embodiment of the invention, which embodiment is given by way of entirely non-limiting example and illustrated by the attached drawings, in which:

FIG. 7F shows an exemplary top perspective view of an embodiment where cam mechanism CM20 are non-movably arranged to second linking arm LA2, and addition radiation source holding arm AA2C holding radiation source XS forming an enclosure with a pin or bolt PIN attached thereto, pin PIN slidably engaging with groove GR, such that radiation source holding arm AA2C can pivot relative to second transversal arm AA2 around pivot point P3.2;

FIG. 10 shows different views of an exemplary handle 300 that can be attached to main rotational arm RA, or other parts of radiation apparatus 100 that can be motor-assisted, having two (2) connection elements 32, 34;

Herein, identical reference numerals are used, where possible, to designate identical elements that are common to the figures. Also, the images in the drawings are simplified for illustration purposes and may not be depicted to scale.

DETAILED DESCRIPTION OF THE SEVERAL EMBODIMENTS

Figure 1:
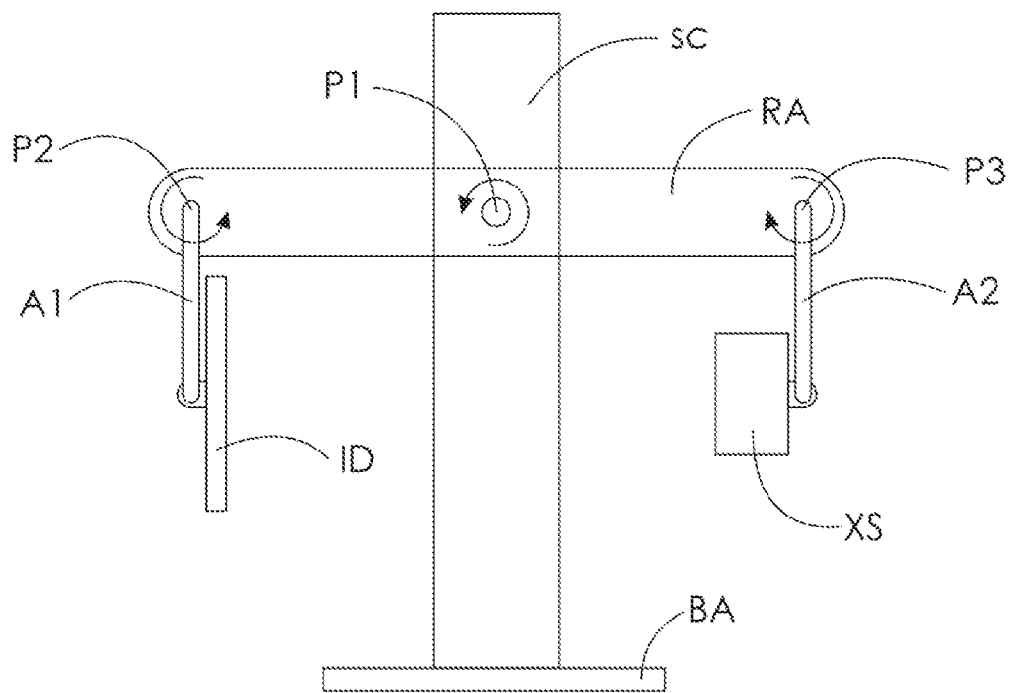
FIG. 1 shows an exemplary side view of a schematic and simplified representation of a radiography apparatus 100, having a base BA, a substantially vertically-arranged support column SC standing on base BA, a main rotatable arm RA that can rotate around a first pivot P1 relative to support columns SC defining an axis of rotation that is perpendicular to a vertical axis of extension of support column SC, main rotatable arm RA exemplarily shown to be perpendicularly arranged relative to support columns SC, main rotatable arm RA also able to slide up and down along support column SC with a slider SLI, a first arm A1 rotatably attached to one side of the rotatable arm RA to rotate about a second pivot P2 holding a radiation imaging device ID, and a second arm A2 rotatably attached to an other side of the rotatable arm RA to rotate about a third pivot P3 holding a radiation source or generator, for example an X-ray device XS.
Figure 2:
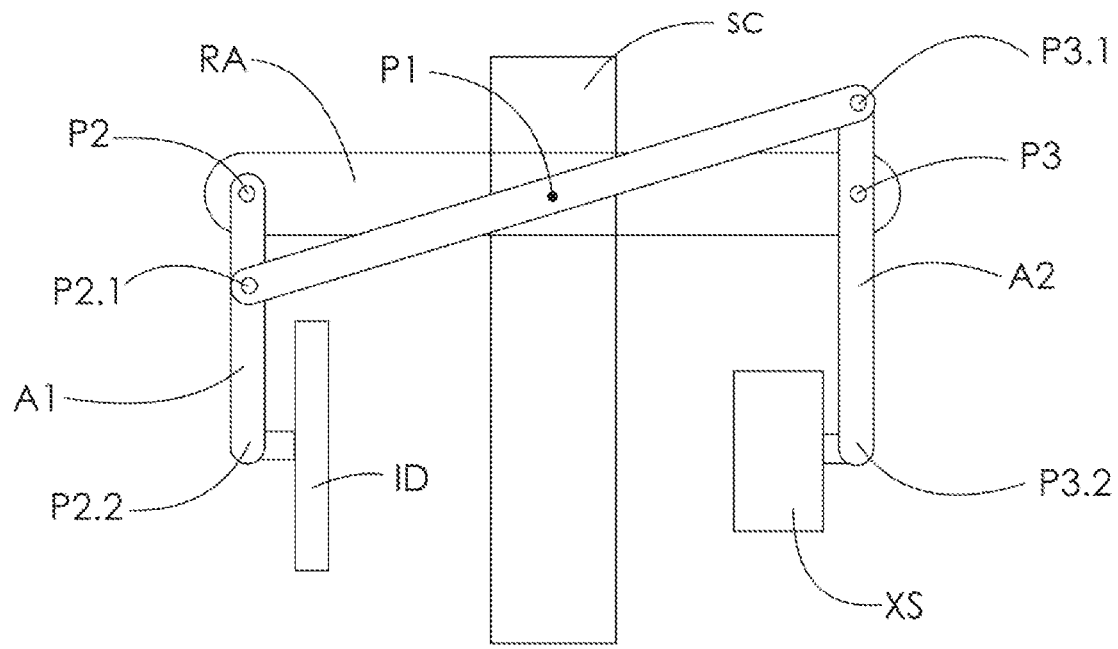
FIG. 2 shows another exemplary side view of a schematic and simplified representation of a radiography apparatus 100 further showing a linking mechanism LM that links a rotation of the first arm A1 to the rotation of the second arm A2, implemented as a transversal bar that is rotatably attached with one end at a location of first arm A1 with pivot point P2.1 between pivot points P2 and P2.2 and that is also rotatably attached with the other end at a location of second arm A2 with pivot point P3.1 at a part of second arm above pivot point P3, such that a rotation of the first arm A1 causes a rotation of the second arm A2 and vice versa, the rotations of A1 and A2 being in opposite rotational directions, allowing for an adjustment of source image-receptor distance (SID), with imaging device ID rotatably attached to first arm A1 at a lower end or side with pivot axis P2.2, and the radiation source XS rotatably attached to second arm A2 at a lower end or side with pivot axis P3.2.

According to one aspect of the present invention, a radiography apparatus 100 is provided, as exemplarily shown in a simplified version for illustration purposes with a side view in FIGS. 1 and 2, having a movable radiation source XS, for example an X-ray source or generator and corresponding X-ray optics, and having a radiation axis RAA, and an imaging device ID, for example an X-ray detector with an imaging plate or flat-panel detector, having an imaging axis IMA and an imaging plane IMP that is perpendicularly arranged to axis IMA. Preferably, imaging axis IMA and radiation axis RAA are substantially coinciding with each other, within a certain angular tolerance or linear deviation, or radiation axis RAA is arranged such that it points to a central location on imaging plane IMP. However, the aspects of the herein described embodiments of the invention are not limited to X-ray applications, as this application is provided as an example, but can also be used for other types of radiation apparatuses, for example but not limited to nuclear medicine devices, dental imaging devices, gamma ray apparatus, general projectional radiography. Radiography apparatus 100 can further includes a base BA for placing apparatus 100 on a floor, a substantially vertically-arranged a device for holding the main rotatable arm RA, for example but not limited to a support column or support post SC attached to a standing base BA, and a main rotatable arm RA that can rotate around a first pivot P1 relative to support column SC. Main rotatable arm RA can be attached to a slider SLI that may allow main rotatable arm RA to move upwards and downwards along a vertical direction along an extension of support column SC. It is also possible that main rotatably arm RA is mounted to another type of device for pivotably holding the main rotatable arm RA, for example a wall bracket, a portion of a wall, a rail, or to another device, and it is also possible that there is no base BA. Also, main rotatable arm RA can be mounted to a wall or other device directly without a support column SC, with or without slider SLI. Main rotatable arm RA is exemplarily shown to be perpendicularly-arranged relative to a vertical extension of support column SC, and has two extending arms or sides away from first pivot P1 that forms a rotational axis for arm RA, first pivot P1 attached to slider SLI.

Moreover, radiography apparatus further includes a first arm A1 that is rotatably attached to one side of the rotatable arm RA to rotate about a second pivot P2 holding a radiation imaging device ID, second pivot P2 allowing first arm A1 to rotate relative to main rotatable arm RA, and a second arm A2 that is rotatably attached to an other side of main rotatable arm RA to rotate about a third pivot P3 holding a radiation source XS, for example an X-ray generator, third pivot P3 allowing second arm A2 to rotate relative to main rotatable arm RA. With this arrangement, it is possible that first arm A1 is turned by a certain angle about pivot P2 in a counter-clockwise direction, and second arm A2 is turned by a certain angle about pivot P3 in a clockwise direction, and thereby approaching imaging device ID and radiation source XS. This allows to reduce a source-imaging distance SID of apparatus 100 by rotational movements, and without the need of linear sliders or other linear motion or guiding arrangements. Conversely, by turning first arm A1 by a certain angle about pivot P2 in a clockwise direction, and turning second arm A2 by a certain angle about pivot P3 in a counter-clockwise direction, a distance between imaging device ID and radiation source XS can be increased.

The source-imaging distance SID can be defined as a distance from a surface of the image detector plane, for example imaging plane IMP, and a position of the radiation source XS. The SID is an factor that a radiography operator, user, radiographer, radiologist, or radiography physician may want to vary manually for changing a magnification of the object that is being imaged, for example a bone structure of a living being or patient. However, it is also possible that the SID is changed by a motor assistance upon engagement by user, or is changed fully automatically by computer instructions and motor assistance. With an increased SID distance, a magnification of the imaged object is reduced, as the radiation that impinges upon the imaging device ID is more spread out on the imaging plane IMP. In other words, a maximal SID distance is used to minimize magnification of the to-be imaged object onto the imaging plane IMP. For example, it may be possible to vary the SID between a predefined SID, for example within an exemplary range between 100 cm and 200 cm. Generally, a patient, living being, or any other object that needs to be imaged by apparatus 100 is placed between imaging device ID and radiation source XS into a propagation path of radiation direction RAA, forming a source-to-object distance SOD from radiation source XS.

Figure 3A:
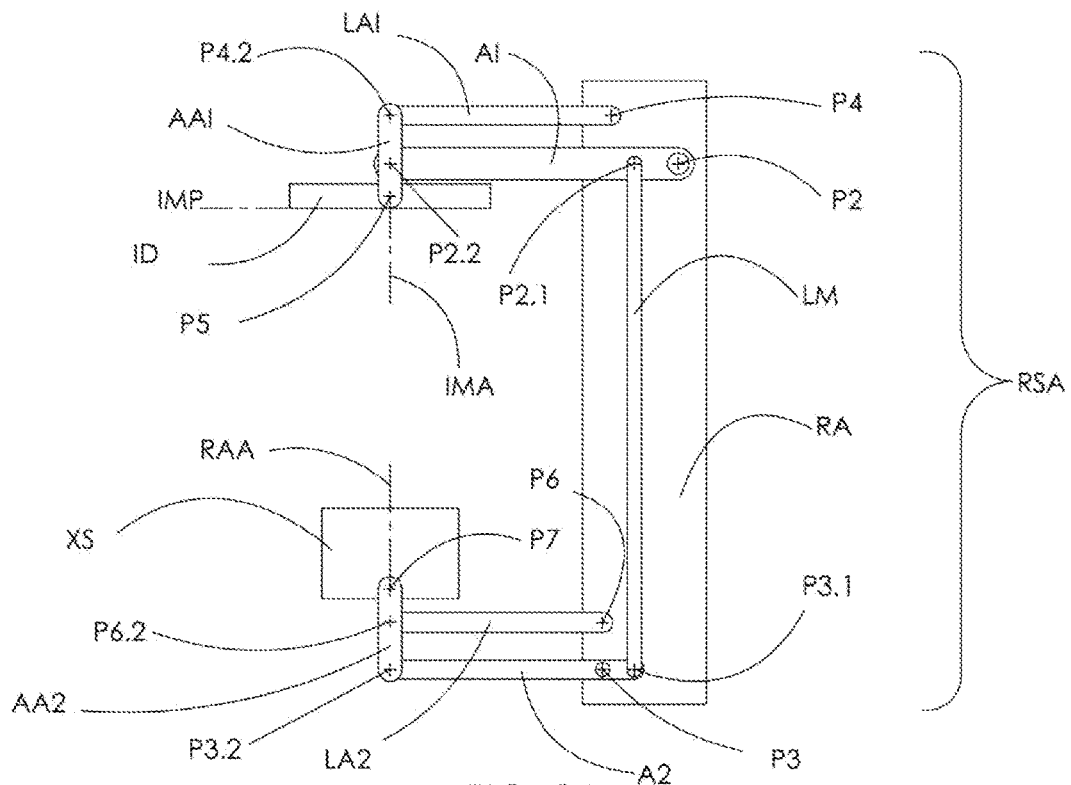
FIGS. 3A to 3D show another aspect of the present invention, showing an aspect of radiography apparatus 100, with FIGS. 3A-3C showing front side views depicting solely the rotational subassembly RSA, and FIG. 3D showing radiography apparatus 100 with rotational subassembly RSA, where an imaging axis IMA of imaging device ID and radiation axis RAA of radiation source XS are arranged to be parallel to each other irrespective of an angular position of first arm A1 relative to main rotatable arm RA and irrespective of an angular position of second arm A2 relative to main rotatable arm RA, or radiation axis RAA being perpendicular to imaging plane IMP, embodied with first and second linking arms LA1 and LA2 that connected to first transversal arm AA1, in this variant an imaging device holding arm, and second transversal arm AA2, in this variant being a radiation source holding arm, respectively, with FIG. 3A showing radiography apparatus 100 without support column SC with main rotatable arm RA arranged vertically, and first arm A1, second arm A2, first linking arm LA1, and second linking arm LA2 exemplarily arranged perpendicularly to main rotatable arm RA, FIG. 3B showing the rotational subassembly RSA where the SID is shorter as compared to FIG. 3A, with first arm A1, second arm A2, first linking arm LA1, and second linking arm LA2 exemplarily arranged obliquely to rotatable arm RA, in both situations imaging axis IMA of imaging device ID and radiation axis RAA of radiation source XS arranged to be in parallel with each other, and FIG. 3C showing rotational subassembly RSA with main rotational arm RA that is obliquely arranged relative to support column SC or a direction of gravitational forces, being exemplarily located at 45°.
Figure 3B:
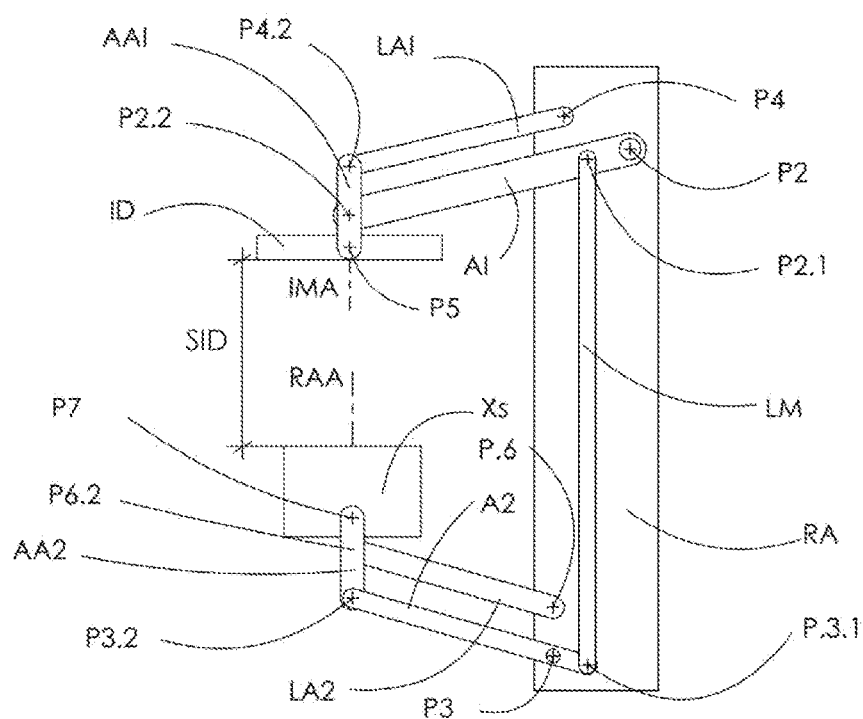

Moreover, with this embodiment, it is possible that imaging device ID can turn relative to first arm A1 within an angular range, or that radiation source XS can turn relative to second arm A2 within an angular range, or both, for example with pivot points P2.2 and P3.2 that can be actuated by electric means, for example a stepper motor or another motor that allows to apply small angular positional changes to a rotational axis, or by passive mechanical means, as further explained with respect to FIGS. 3A and 3B, such that radiation axis of radiation source XS can lie within imaging plane of imaging device ID. This allows a user to vary a SID by rotation of one or both arms A1, A2, while at the same time ascertaining that radiation imaging can be performed.

With this arrangement described in FIG. 1 where a first arm A1 holding an imaging device ID and second arm A2 holding a radiation source XS are pivotable to reduce or lengthen the SID, it is possible to avoid linear guiding and motion mechanisms that are expensive, require very clean conditions, and also require regular maintenance. In addition, any encapsulation or enclosures that are complex and require regular cleaning are avoided, as simply sealed ball bearings with bolts can be used for the rotational axes. Moreover, there are other advantages to replace linear guiding and motion mechanisms with rotative joints or pivots. For example, generally, the mechanical embodiments of rotation with an axis having bolt or shaft with a ball bearing is cheaper and more reliable as compared to the use of a linear motion axis. This is a result of the mechanical reduction caused by arms A1, A2 acting as torque levers that are coupled with a rotative motion around pivot points P2, P3, respectively, that is absent with a linear motor or guiding mechanism. For example, a rotative length RD1, RD2, of arms A1, A2, respectively can be chosen to be exemplarily in the range of 300 mm to 600 mm, whilst a diameter of ball bearing and a bolt, rod, shaft that forms rotational axes P2, P3 can be less than 30 mm, leading to a gearing reduction of at least a factor 10 or more. Also, a comparable liner motional range that is implemented with rotational arms and pivot points is generally cheaper than a linear motor or linear guiding structures.

In addition, at least in some application fields for the herein presented radiation apparatus and system, the environmental conditions are more humid and more dusty as compared to radiation locations in classic hospitals or other health care premises. By using conventional sealed ball bearings to support the different pivot points, for example built for complying with IP66, IP67 or even IP68 protection category based on IEC standard 60529, it is possible to seal the movable parts and the arms A1, A2, RA, and other rotative elements by inexpensive and simple means, as compared to the requisite sealing grades of linear motor or linear guiding structures.

Rotative ball bearings that are sealed can also have a substantially longer and maintenance free product life cycle, and will not need to be replaced for many years, in particular in the present situation where the rotations performed at pivot points P1, P2, P3, are only small angular variations of arms A1, A2 relative to main rotational arm RA, and main rotational arm RA versus support column SC. In the case of linear guiding structures and motion, maintenance with cleaning and re-greasing will have to be performed at more frequent intervals.

FIG. 2 shows a side view of a simplified and exemplary radiation apparatus 100 according to another aspect of the present invention, where additional mechanical elements permit a manual variation of the SID between imaging device ID and radiation source XS. Specifically, in this embodiment, a linking means between the first and second arm A1 and A2 is provided to couple a rotation of arm A1 to arm A2 and vice versa, in the form of a linking mechanism LM that is embodied as a transversal bar. Linking mechanism LM operatively interconnects the first arm A1 with the second arm A2, such that a clockwise-rotation of first arm A1 around second pivot P2 will cause a counter-clockwise rotation of second arm A2 around third pivot P3, and vice versa. This allows a radiation operator or user to manually operate only one arm, either first arm A1 or second arm A2, to modify the SID, and the other arm that has not been moved will follow. In addition, the coupling of the rotational movements of arms A1 and A2 by linking mechanism LM allows to ascertain that imaging axis IMA and radiation axis RAA remain substantially aligned. With linking mechanism LM, a simple mechanical arrangement is provided that allows to mechanically couple rotational movements of first and second arms A1, A2 together, for example for varying the SID, and also at the same time allows to provide for a mechanism that maintains an alignment between imaging axis IMA and the radiation axis RAA.

In the variant shown, one end or extremity of linking mechanism LM is rotatably attached to first arm A1 with a pivot point P2.1 between second pivot point P2 and a location where imaging device ID is attached to first arm A1, and the other end or extremity of linking mechanism LM is rotatably attached to second arm A2 with a pivot point P3.1 that is arranged away from third pivot point P3, in the variant shown above third pivot point P3 at an extension of second arm A2. In the variant shown, linking mechanism LM is shown to include a transversal bar, rod, rail, strut that is arranged obliquely to an extension of main rotational arm RA. However, it is also possible that the locations of attachment and pivot points P2.1 and P3.1 are reversed for first and second arms A1, A2. Moreover, imaging device ID is attached via a transversal holding arm AA1 with a pivot point P2.2 that allows for a rotation of first transversal holding arm AA1 with imaging device ID relative to first arm A1, and radiation source XS is attached via a second transversal arm AA2 with a pivot point P3.2 that allows for a rotation of second transversal holding arm AA1 with source XS relative to second arm A2. In the variant shown, first transversal holding arm AA1 is arranged to be substantially coinciding with imaging axis IMA, and second transversal holding arm AA2 is arranged to be substantially coinciding with radiation axis RAA. Moreover, pivot point P2.1 where linking mechanism LM is attached to first arm A1 is located between pivot points P2 and P2.2.

This embodiment with linking mechanism LM shows another advantage of the herein presented radiation device or system, allowing for a simple and inexpensive mechanical coupling of one rotative motion of the first arm A1 with another rotative motion of the second arm A2, as compared to a cumbersome, difficult, and even impracticable mechanical coupling of a motion of two different linear motion structures. In addition, by choosing the weights of the subassembly including first arm A1 and imaging device ID, and the subassembly including second arm A2 and radiation source XS, a torque caused by one assembly around pivot point P2 can reduce or even substantially cancel a torque caused by the other assembly around pivot point P3. It would be substantially more complex and costly to provide such weight balancing advantage with linear guiding structures, if not impossible.

Figure 3C:
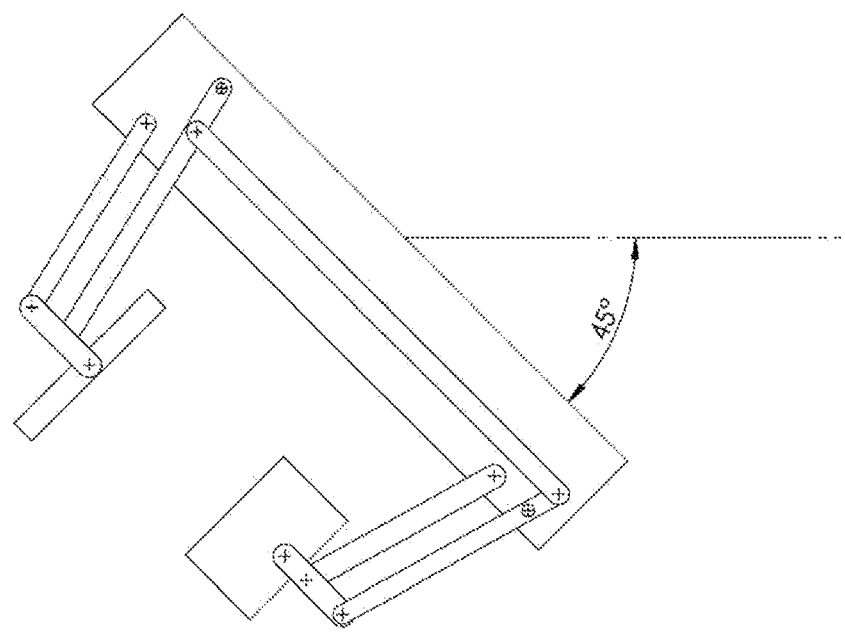
Figure 3D:
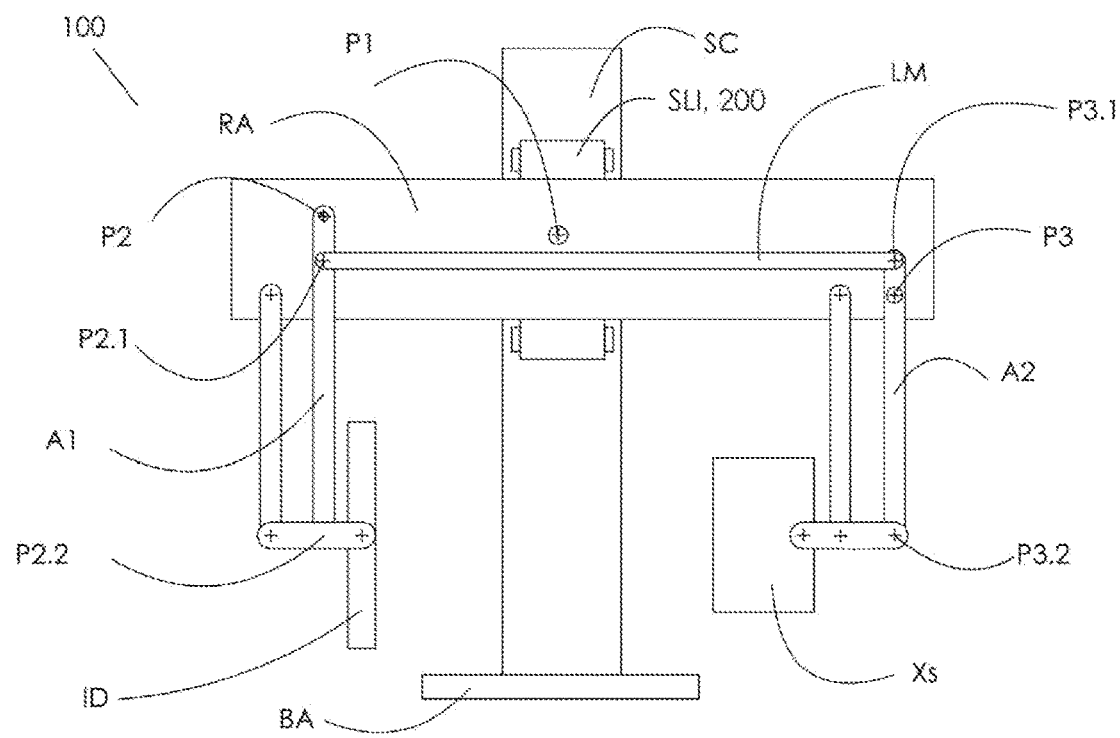
Figure 6A:
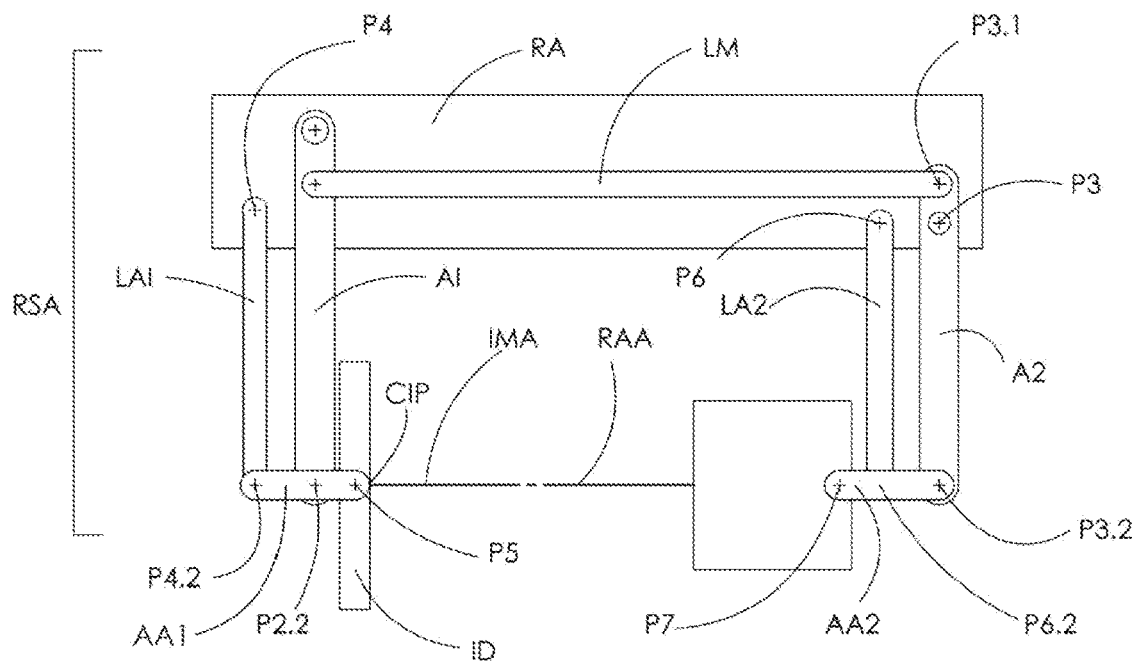
FIG. 6A to 6B show another aspect of the present invention, showing a simplified version of rotational subassembly RSA, where a first linking arm LA1 is at one end pivotably attached to main rotational arm RA with pivot P4, LA1 attached pivotably at the other end to a first appliance holding arm AA1 with pivot point P4.2, that is in turn attached to imaging device ID, and a second linking arm LA2 is at one end pivotably attached to main rotational arm RA with pivot P6, LA2 attached pivotably at the other end to a second transversal arm AA2 with pivot P6.2, in this variant radiation source XS attached to second transversal arm AA2, such that first linking arm LA1 and first arm A1 form a first parallelogram mechanism 1PM and second linking arm LA2 and second arm A2 form a second parallelogram mechanism 2PM, the first and second parallelogram mechanisms are configured such that an optical axis RAA of the X-ray source forms a fixed angle within a certain angular range relative to an imaging plane IMP formed by the X-ray imaging device, irrespective of an angular position of first and second arm A1, A2, with FIG. 6A showing first and second arms A1 and A2 in an exemplary vertical position, and FIG. 6B showing first and second arms A1 and A2 in an oblique position relative to main rotational arm RA.
Figure 6B:
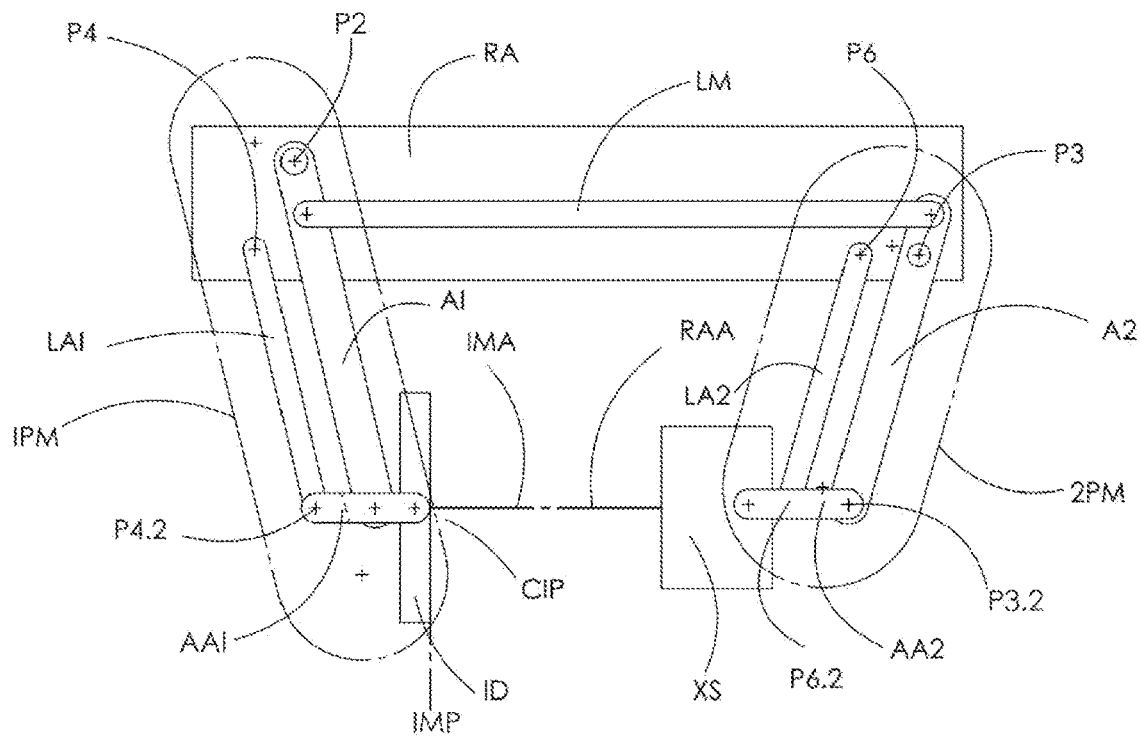

FIGS. 3A to 3C show another aspect of the present invention, with more details shown in FIGS. 6A and 6B showing the rotational subassemblies RSA without the support column SC, depicting an exemplary and simplified radiography apparatus 100 from a side view, where main rotational arm RA of rotational subassembly is vertically arranged, or is arranged parallel to a direction of gravitational forces, and where a first parallelogram mechanism 1PM and a second parallelogram mechanism 2PM are shown, such that imaging axis IMA of imaging device ID and radiation axis RAA of radiation source XS will be arranged at a fixed angular relationship to each other, irrespective of an angular position of first arm A1 relative to main rotatable arm RA, and irrespective of an angular position of second arm A2 relative to main rotatable arm RA. Generally, imaging axis IMA of imaging device ID and radiation axis RAA of radiation source XS are arranged to be parallel to each other within a certain angular range, or even substantially coincide with each other. First parallelogram mechanism 1PM is embodied with a linking arm LA1 that is arranged to be parallel to first arm A1, linking arm LA1 pivotably attached at one end to main rotational arm RA with pivot point P4, and pivotably attached to the other end to an extending portion of first transversal holding arm AA1 with a pivot point P4.2. Second parallelogram mechanism 2PM arranged opposite to first parallelogram mechanism 1PM is embodied with a linking arm LA2 that is arranged to be parallel to second arm A2, linking arm LA2 pivotably attached at one end to main rotational arm RA with pivot point P6, and pivotably attached to the other end to an extending portion of second transversal holding arm AA2 with a pivot point P6.2.

The four (4) pivot points of first and second parallelogram mechanisms 1PM, 2PM are arranged with relative geometrical distances to each other such that rotational or angular motion to arm A1 will not change an orientation of imaging device ID, more precisely an orientation of imaging axis IMA or the perpendicularly arranged imaging plane IMP, and such that a rotational or angular motion to arm A2 will not change an orientation of radiation source XS, more precisely an orientation of radiation axis RAA. For example, a distance between pivot point P4.2 and P4 of the extremities of linking arm LA1 is the same distance as between pivot point P2.2. and P2 of first arm A1. In addition, a distance between pivot point P6.2 and P6 of the extremities of linking arm LA2 can be the same distance as between pivot point P3.2. and P3.1 of second arm A2. Moreover, a line formed by pivot points P4.2, P2.2, and P5 along first transversal holding arm AA1 is parallel to a line formed by pivot points P2, P4 that are located on main transversal arm RA, and a line formed by pivot points P6.2, P3.2, and P7 along second transversal holding arm AA2 is parallel to a line formed by pivot points P3.1 and P6 located on main transversal arm RA. FIG. 3B as wells as FIG. 6B showing a situation where the SID is shorter as compared to the SID of FIG. 3A and FIG. 6A, respectively, with first arm A1, second arm A2, linking arm LA1, and linking arm LA2 exemplarily arranged obliquely to main rotatable arm RA, in both situations imaging axis IMA of imaging device ID and radiation axis RAA of radiation source XS are arranged to have a fixed angular relationship to each other, for example to be substantially in parallel to each other, within a certain angular range. Consequently, radiation axis RAA is arranged to have a fixed angular relationship relative to imaging plane IMP, for example to be substantially perpendicular to imaging plane IMP within a certain angular range, for example in a range between ±3°, irrespective of an distance SID, as shown in FIGS. 3A and 3B, and also shown in FIGS. 6A and 6B. FIG. 3C shows a front view of a rotational subassembly RSA of a radiation apparatus, where main rotational arm RA is arranged at 45° off its horizontal position in an oblique position, or 45° off from a direction of gravity.

According to another aspect, it is also possible that a rotation blocking and unlocking mechanism is provided, operative around pivot point P5 between imaging device ID and first transversal holding arm AA1, for example an eccentric cam and lever blocking mechanism, that can lock a rotation or turning of imaging device ID around pivot point P5, but can, when released, allow for a certain angular rotational range of imaging device ID relative to first transversal holding arm AA1. Generally, imaging axis IMA and radiation axis RAA are arranged to coincide with each other as exemplarily shown in FIG. 3A. However, it is then possible to release cam and lever blocking mechanism, so that an angle of imaging axis IMA relative to an axis of extension of first transversal holding arm AA1 can be changed. Thereby, it is possible to illuminate or radiate imaging plane IMP of imaging device ID with radiation at a non-perpendicular angle, for example for oblique radiation imaging.

Moreover, according to another aspect of the present invention, a mechanism is provided that is operatively attached between the linking mechanism LM and main rotational arm RA, herein referred to as spring load mechanism SLM, the SLM including a spring SP or other spring-like device that can store mechanical energy. The SLM is schematically and exemplarily shown in FIGS. 4A and 4B. Spring load mechanism SLM is configured such that spring SP is tensioned when first arm A1 and second arm A2 are arranged to be parallel to each other (for example as shown in FIG. 6A), and is configured such that spring SP progressively releases tension when (i) first arm A1 and second arm A2 are rotated or turned away from each other when increasing the SID, and when (ii) first arm A1 and second arm A2 are rotated or turned towards each other when decreasing the SID (for example as shown in FIG. 6B). This allows to compensate for the weight of the assemblies of both first and second arm A1 and A2 and the devices and elements attached thereto, that will have a tendency to urge towards a lowest potential energy position based on the effects of gravity. In the variant shown in FIG. 6B, where main rotational arm RA is horizontal, and first and second arms A1, A2 are not arranged in the vertical position but are obliquely arranged towards one another, without any brake or stopping mechanism or other mechanical compensation, first and second arms A1, A2 would revert back to a vertically-extending position based on the effects of gravity, to take the position as shown in FIG. 6A.

Figure 4A:
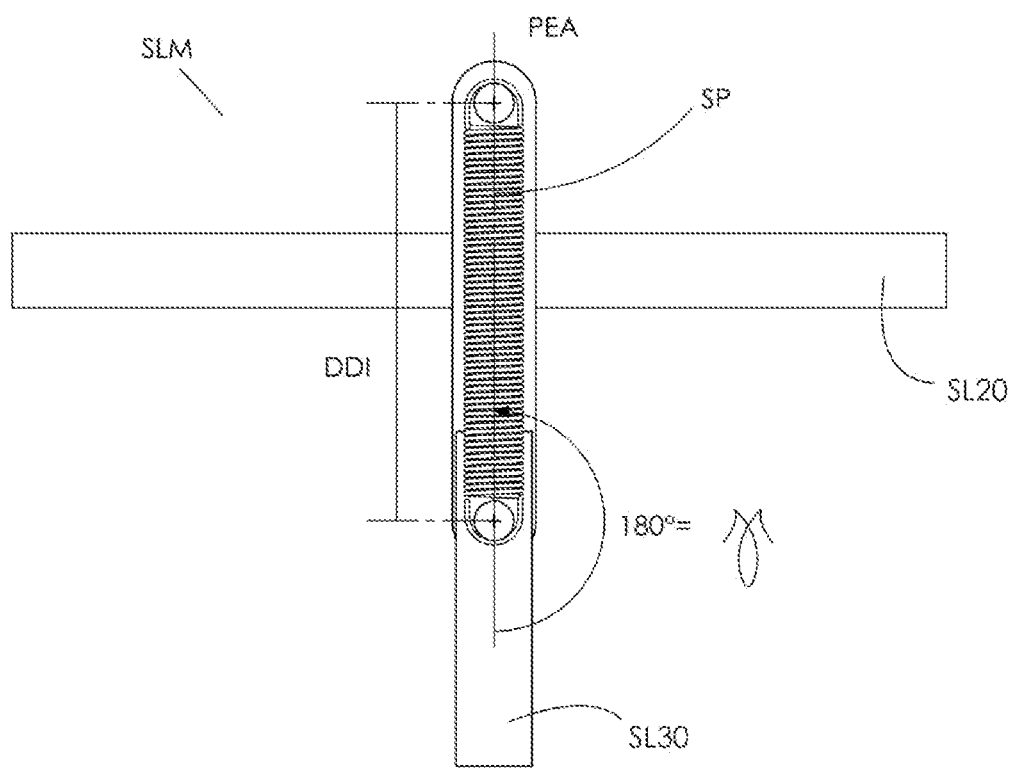
FIGS. 4A to 4G show different views of a spring load mechanism SLM and angle compensation mechanism ACM, and two graphs representing torques and forces, with SLM having a spring that acts on the linking mechanism LM in a situation where main rotatable arm RA is not in a vertical position, and first and second arm A1, A2 are also not in a vertical position, the spring load mechanism SLM configured such that spring SP is tensioned when first arm A1 and second arm A2 are parallel to each other as shown in FIG. 2 with a length DD1, and configured such that spring SP progressively releases tension when first arm A1 and second arm A2 are rotated away from each other when increasing or decreasing SID with spring SP having a length DD2 that is shorter than DD1, with FIG. 4A showing spring load mechanism SLM with spring SP in a most tensioned state, FIG. 4B showing spring load mechanism SLM with spring SP in a de-tensioned or relaxed state, FIG. 4C showing an angle compensation mechanism ACM that is configured to change a tension of spring SP based on an angle between main rotational arm RA and support column SC, that is operatively connected to an axis formed by first pivot P1, the angle compensation mechanism configured to progressively de-tension spring SP of the spring load mechanism by displacing an attachment point P8.3 of spring SP when the main rotatable arm RA is moved from a horizontal position to a vertical position, such that the spring is fully or at least partially de-tensioned when RA is parallel to SC, i.e. in the vertical position, the right side of showing a representation of radiation apparatus with arm RA perpendicular to support column SC, FIG. 4D showing angle compensation mechanism AMC that is acting on an attachment point P8.3 to shorten a tensioning of spring SP, in the case where arm RA is parallel to support column SC, such that no force or torque compensation by spring load mechanism SLM is needed, and FIG. 4E showing a perspective top view of an exemplary integration of spring load mechanism SLM and angle compensation mechanism ACM to radiography apparatus 100, with bar SL20 operatively connected or integrated to linking mechanism LM, FIG. 4F showing different torques that are applied to first and second arms A1, A2 with and without torque or force compensation by spring SP, and FIG. 4G showing different forces that are applied to first and second arms A1, A2.
Figure 4B:
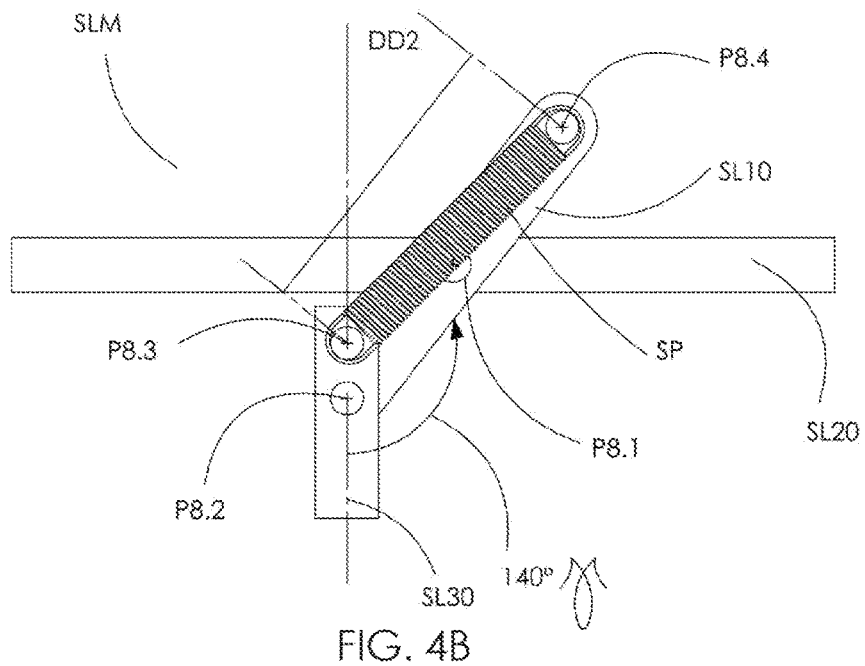

In this respect, as shown in FIGS. 4A and 4B, spring load mechanism SLM includes a spring SP that is attached at an upper end with an attachment point P8.4 to a tilting bar SL10, and is also attached at lower end with an attachment point P8.3 to a movable holder SL30. Tilting bar SL10 is pivotably attached at a lower end or extremity to movable holder SL30, such that pivoting point P8.2 is arranged below attachment point P8.3 to movable holder SL30. This forms a movable triangle formed by points P8.4, P8.3 and P8.2, that can be changed based on a state of expansion or contraction of spring SP. Moreover, tilting bar SL10 is also pivotably attached to a transversal bar SL20 with a pivot point P8.1, that in turn can be attached to linking mechanism LM.

FIG. 4A shows a state of spring load mechanism SLM when radiography apparatus 100 is arranged such that first and second arms A1, A2 are parallel to each other, as exemplarily shown in FIG. 6A. In this state, spring SP is tensioned to a maximal possible extension DD1, and is storing mechanical energy. This is because an angle γ between a longitudinal extension of tilting bar SL10 and a longitudinal extension of movable holder SL30 is 180°, in other words tilting bar SL10 is not tilted. Tilting bar SL10 is arranged to coincide with axis PEA that is perpendicular to an axis of extension of rotational arm RA. Transversal bar SL20 is mechanically affixed to linking mechanism LM, such that any turning or rotational motion to first or second arm A1, A2 will in turn will cause a lateral displacement of the bar or rod that forms linking mechanism LM, which then will in turn will apply a tilting angle to tilting bar SL10.

This is shown in FIG. 4B, where transversal bar SL20 has moved to the right of the illustration, corresponding to the movements of arms A1 and A2 to approach each other to shorten the SID, and the consequential movement of linking mechanism LM to the right, as illustrated in FIG. 6B, by virtue of pivot point P8.1 that pivotably attaches transversal bar SL20 and linking mechanism LM to tilting bar SL10. Tilting angle γ between a longitudinal extension of tilting bar SL10 and a longitudinal extension of movable holder SL30 is shown to be about 140°, and this tilting in turn as reduced a distance between attachment points P8.3 and P8.4 of spring SP to a distance DD2 that is shorter than DD1. In other words, spring SP has released energy, and the energy release causes a first pushing force to linking mechanism LM by virtue of the further contracting spring SP from the initial, more expanded state shown in FIG. 4A with tilting angle being 180°. This first pushing force will act against a pulling force that will is exerted to linking mechanism LM due to the gravity that acts on the weights of the elements that form first and second arms A1, A2 when obliquely arranged towards one another, e.g. not arranged parallel towards each other.

Not shown in FIGS. 4A and 4B, it is also possible that first and second arms A1, A2 are moved away from each other to increase the SID distance. This will move the linking arm LM to the left side of the exemplary illustration of FIG. 6A, and turn will also move transversal bar SL20 to the left. Analogously to the situation of FIG. 4B, and in light of the axi-symmetrical construction of spring load mechanism SLM, the movement of transversal bar SL20 to the left will tilt the tilting bar SL10 by a certain tilting angle γ, and in turn will shorten distance DD1 to a shorter value releasing energy and providing for a pushing force to transversal bar SL20 to the left, for example DD2, that can compensate for the effects of gravity on arms A1, A2 acting on linking mechanism.

Figure 4C:
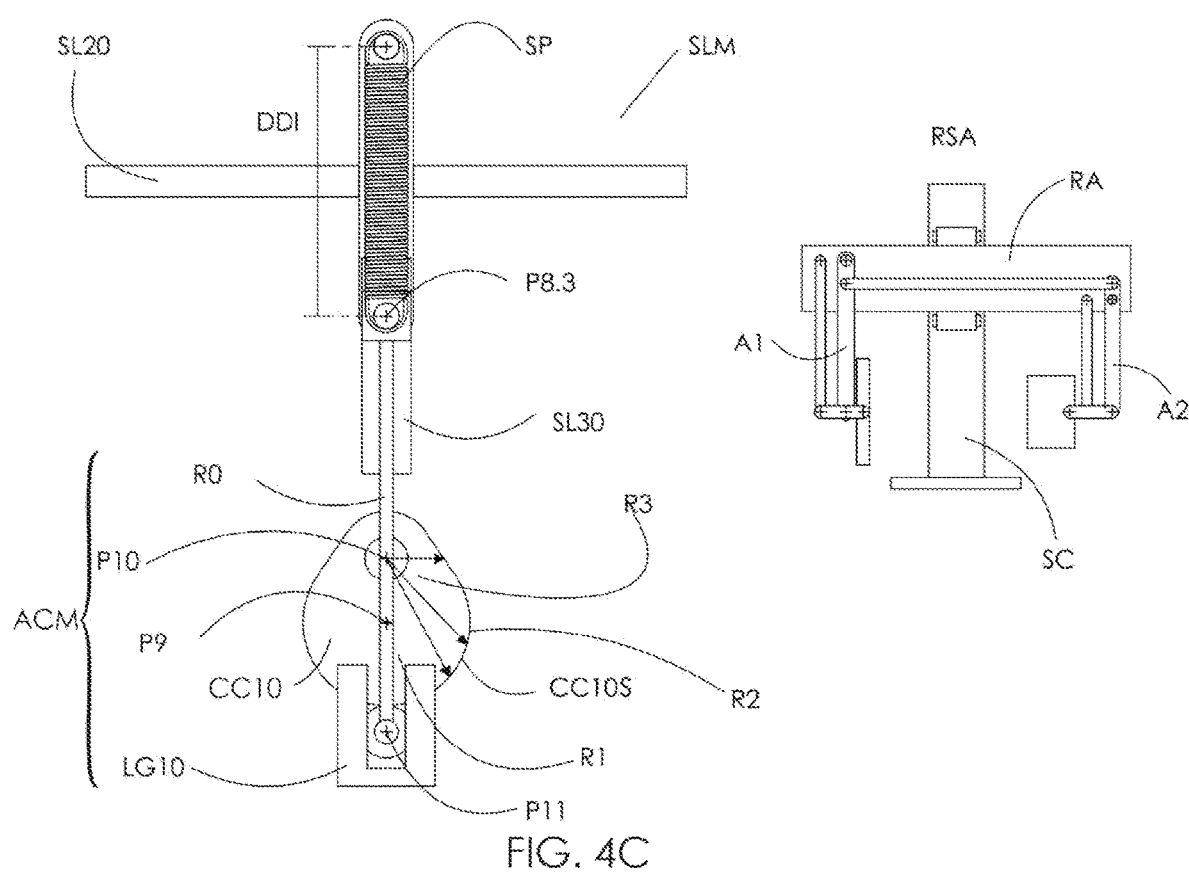
Figure 4D:
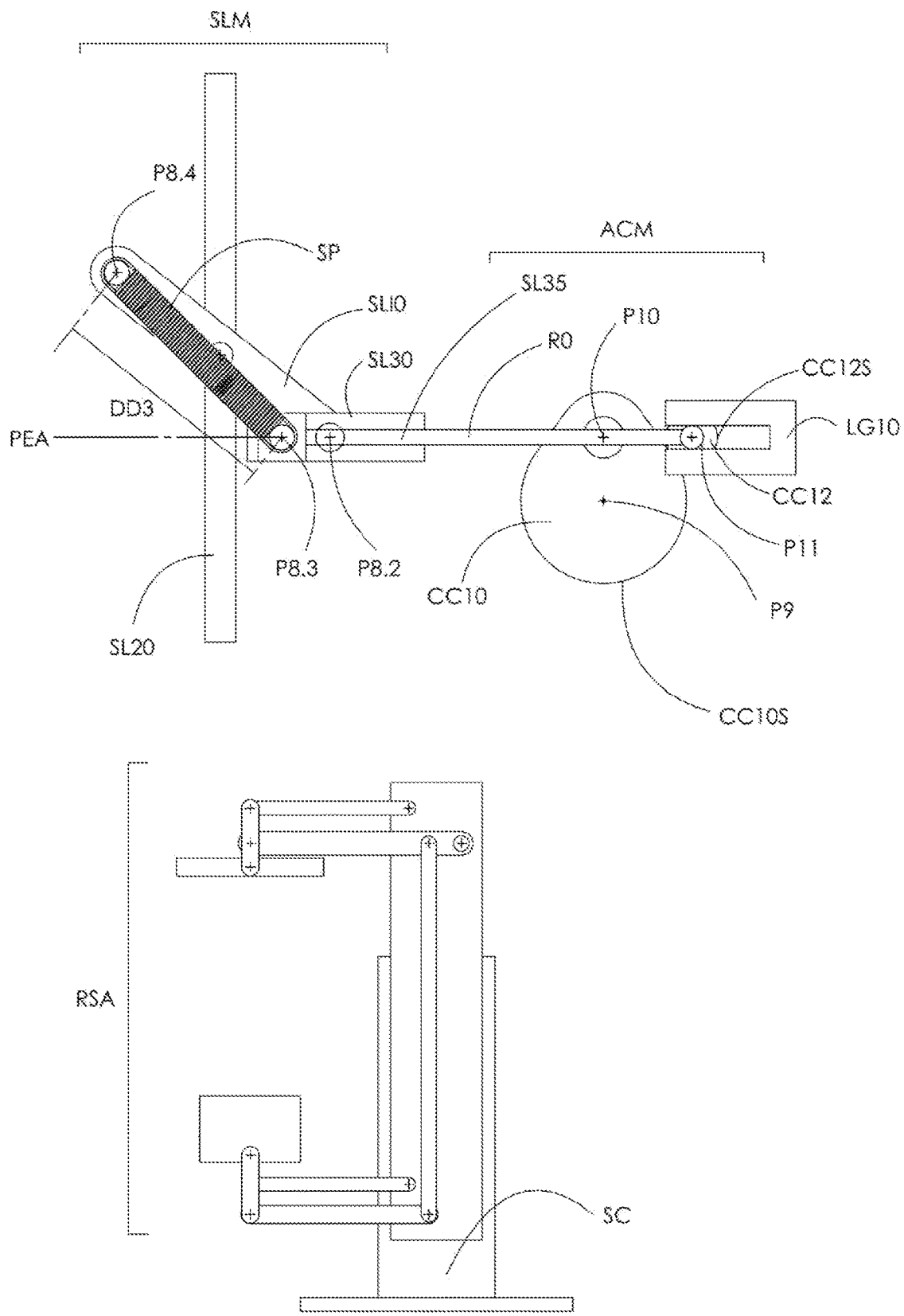
Figure 4E:
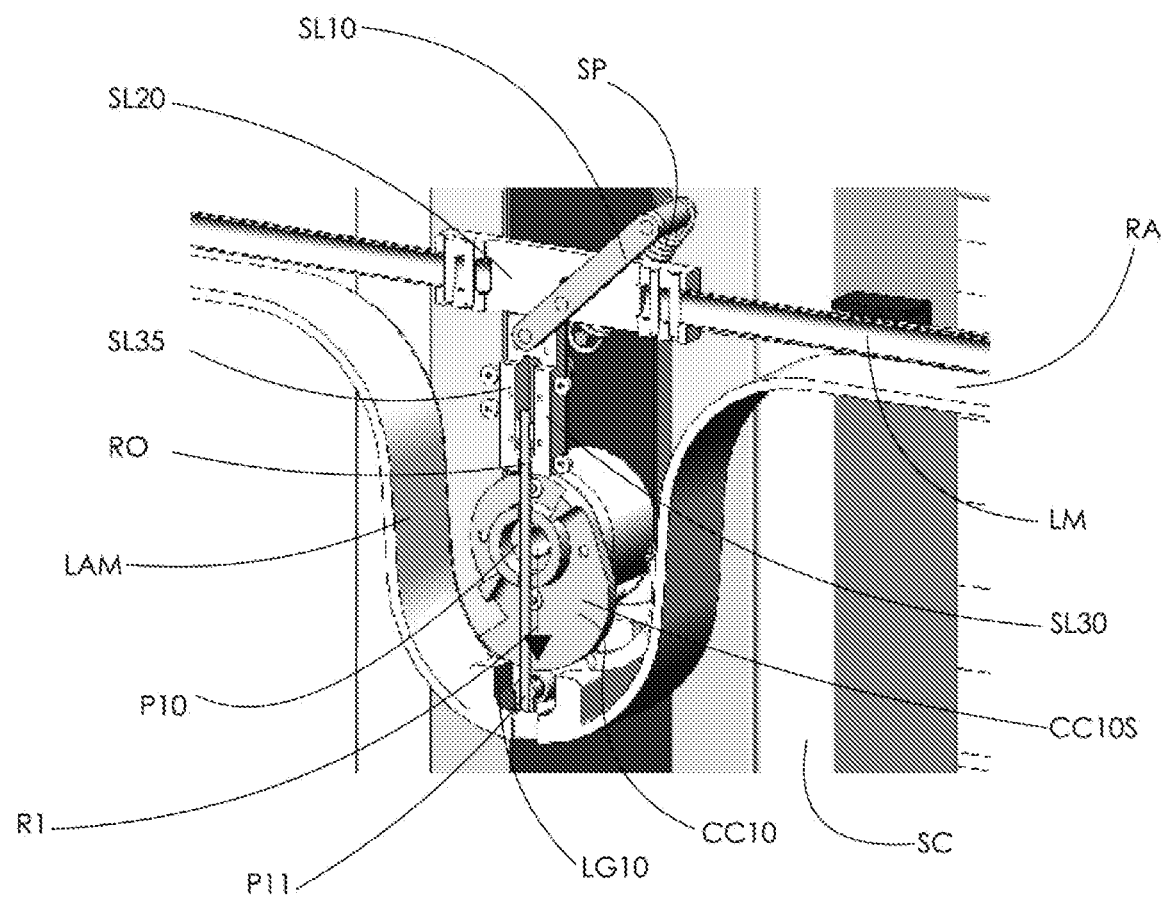
Figure 4F:
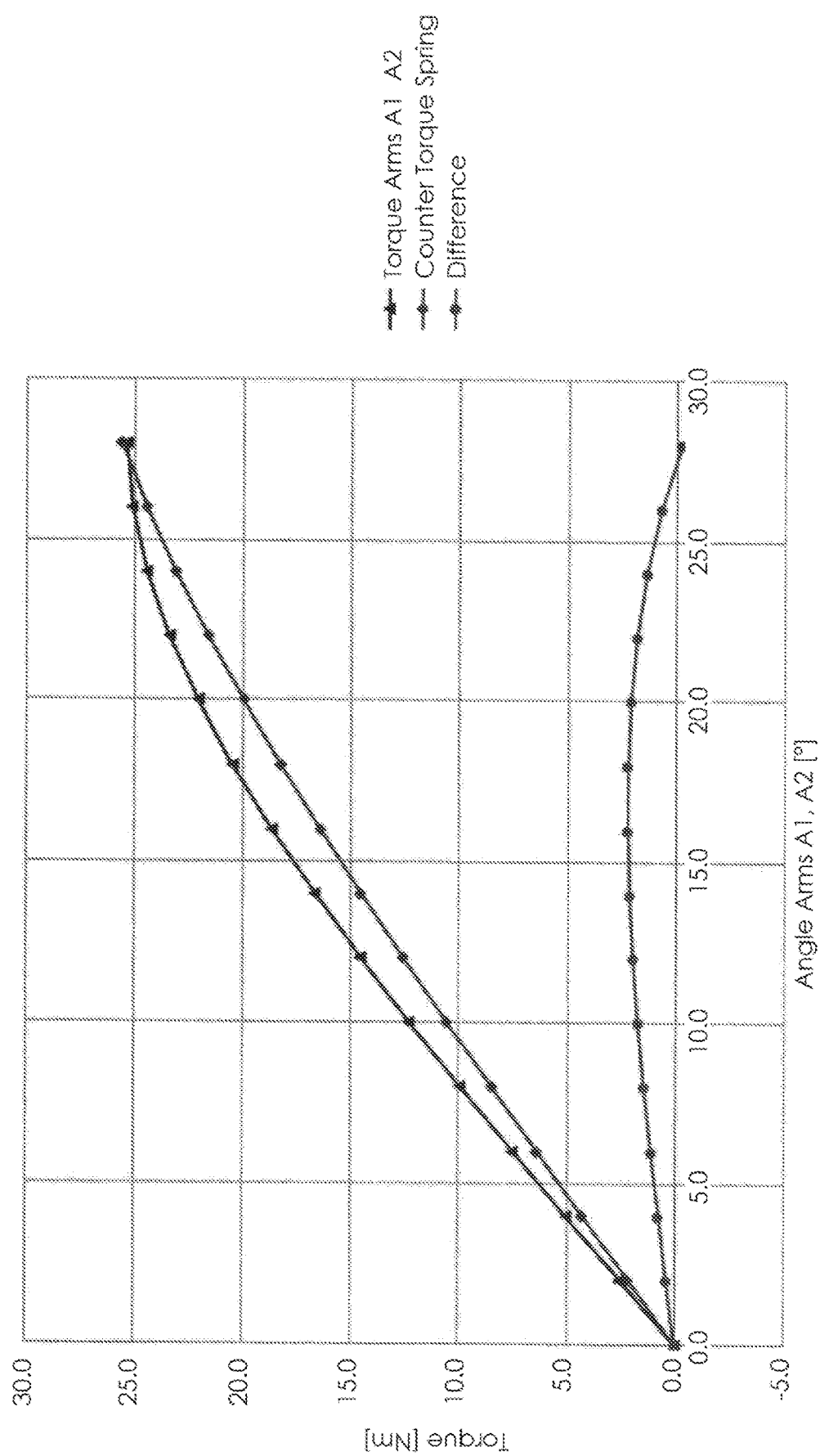
Figure 4G:
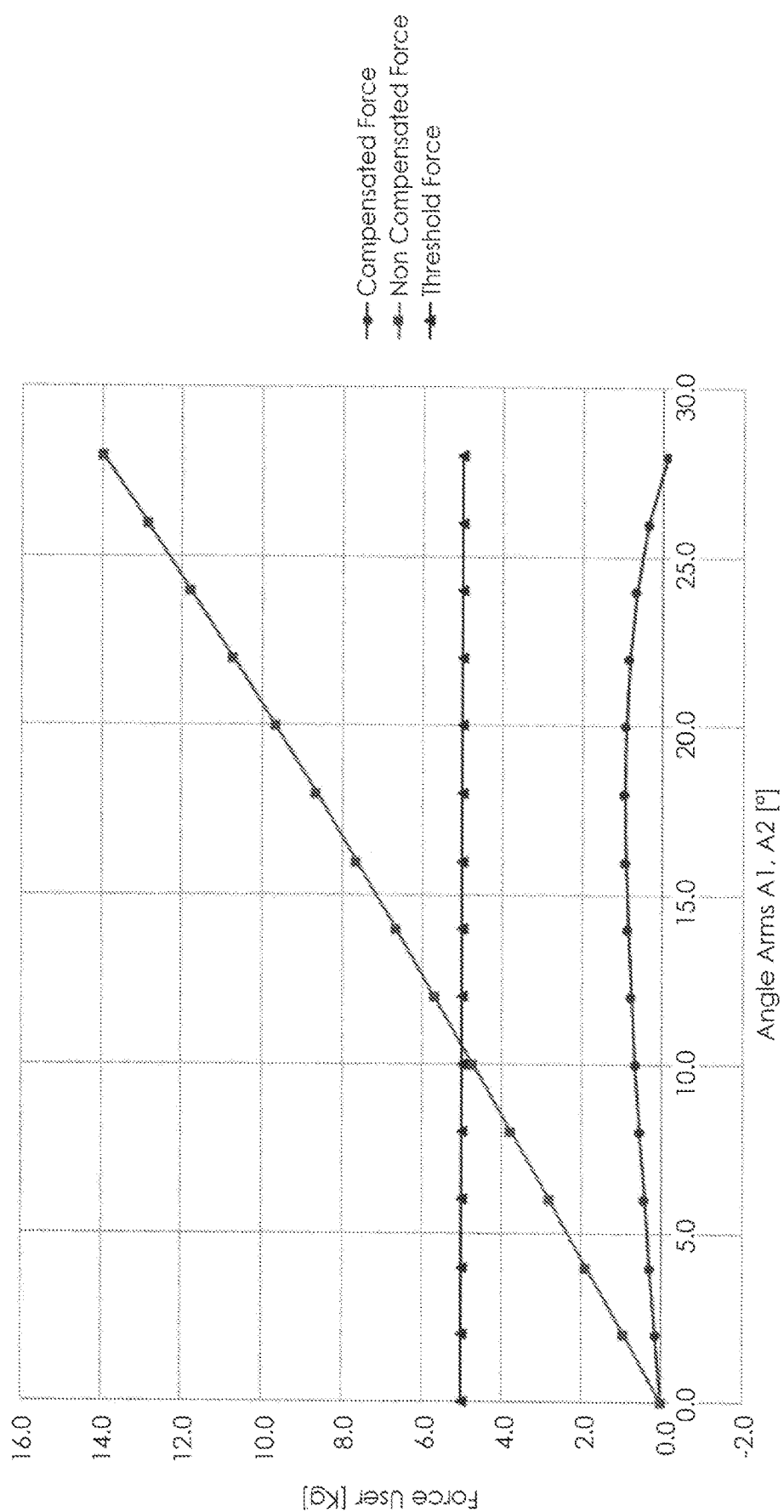
Figure 7A:
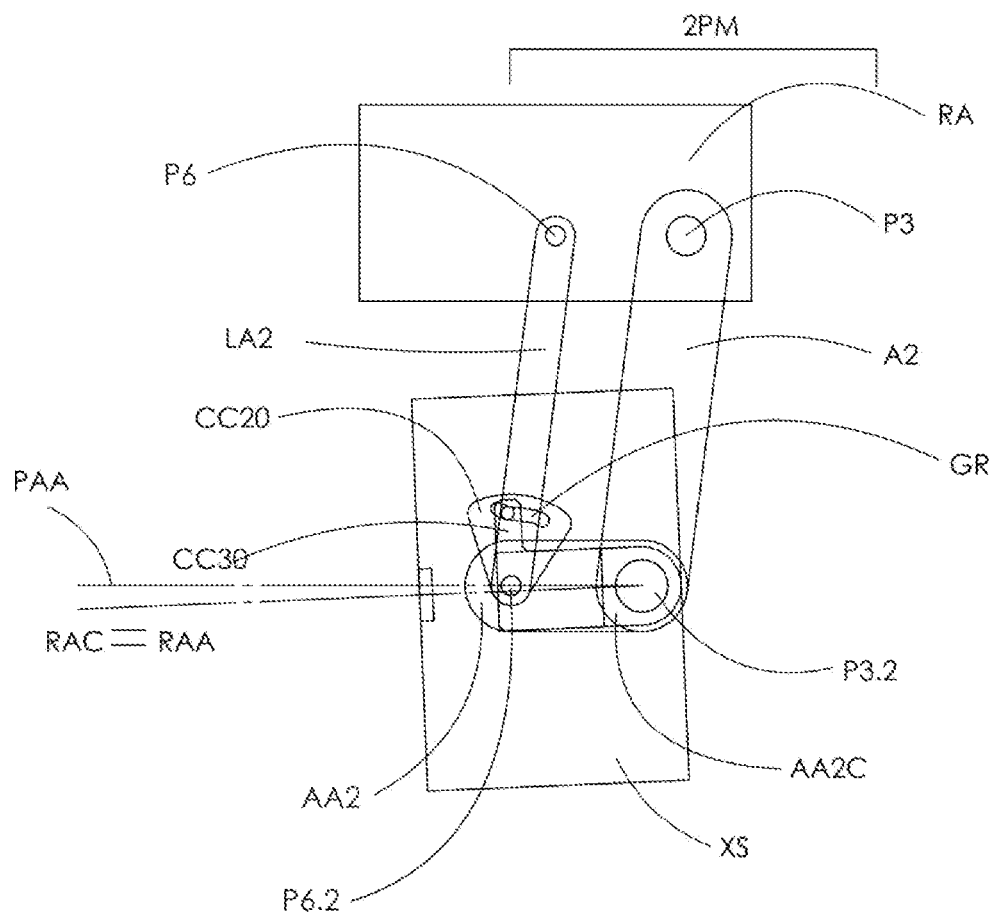
FIGS. 7A to 7F show yet another aspect of the present invention, where and a first distance RD1 between an imaging axis IMA and pivot point P2 of first rotational arm A1 is different than a second distance RD2 between radiation axis RAA and pivot point P3 of second rotational arm A2, and where a cam mechanism CC20 with groove GR, and a pin mechanism CC30 with pin, bolt, or rod PIN is provided for changing an angle of radiation axis RAA of radiation source XS or an angle of orientation of an imaging plane IMP of imaging device ID relative to main rotatable arm RA, cam mechanism CC20 with groove GR, and pin mechanism CC30 with pin PIN arranged and configured such that radiation axis RAA of radiation source XS points towards a center location of an imaging plane IMP of imaging device ID irrespective of the angle between arms A1, A2, with FIG. 7A showing a side view of an exemplary embodiment of second parallelogram mechanism 2PM with cam mechanism CC20, pin mechanism CC30, and additional addition radiation source holding arm AA2C, FIG. 7B showing a top perspective view, and FIG. 7C showing a exploded view thereof, FIG. 7D showing exemplarily first and second arms A1 and A2 in parallel to each other, with pin PIN located slidably within groove GR at a non-compensating position, and with FIG. 7E exemplarily show in first and second arms A1 and A2 in oblique to each other, with pin PIN located slidably within groove GR at an angularly compensating position and limiting the SID distance and motion of arms A1, A2 by pin PIN abutting at an end of groove GR.

Spring parameters of spring SP are designed such that the pushing force established by spring SP to linking mechanism LM and a pulling force created by gravity on arms A1, A2, to linking mechanism LM are approximated, so that the arms A1, A2 can be put to different angular positions to shorten or lengthen the SID, so that a force or equivalent torque that has to be provided by operator, user, or radiographer is relatively small, preferably below 5 kg, as shown in FIG. 4G. Without the compensation, the force needed can exceed 10 kg, for example 14 kg at an angle of 28° as shown as an example. In other words, assuming main radiation arm RA is not arranged to be vertical, for example in a horizontal position as shown in FIG. 7A, weights of arms A1, A2 and all the elements arranged with arms A1, A2, for example imaging device ID and radiation source XS create a torque acting around pivot points P2 and P3, when arms A1, A2 are not arranged perpendicular to an axis of longitudinal extension of radiation arm RA. This torque that is applied to arms A1, A2 can be at least partially compensated by a counter torque that will be applied to arms A1, A2, by force crated by spring SP.

Another aspect of the present invention is illustrated in FIGS. 4C to 4E, where a mechanism is shown that can linearly move movable holder SL30 up and down, as a function of an angular position of main transversal arm RA relative to support column SC, or relative to a direction of the gravitational force, hereinafter referred to as an angle compensation mechanism ACM. For example, in a case where main transversal arm RA is arranged to be vertical, in other words parallel to gravitational forces, a first torque applied around second pivot P2 by a weight of assembly of first arm A1 can be cancelled out by a second torque applied by a weight of the assembly of second arm A2 around third pivot P3, via linking mechanism LM. A turning or rotational motion to any one of first or second arms A1, A2 will not change this equilibrium of the two torques. This situation is illustrated in FIGS. 3A and 3B, and also illustrated in the bottom section of FIG. 4D. This means that a gravitational force that applies to the assembly of the first arm A1 can be compensated by a gravitational force that applies to the assembly of the second arm A2, as they will move in opposite directions due to the linking mechanism LM. This also signifies that the compensatory forces provided by spring load mechanism SLM are not needed, when main transversal arm RA is arranged to be vertical, or when imaging axis IMA and radiation axis RAA are vertical.

However, as soon as main rotational arm RA takes a non-vertical position, for example by progressively moving from the vertical position towards a horizontal position, the effects of the gravity on the assemblies of the first and second arm A1, A2 will increase, these effect will cause a torque to each arm urging first and second arm A1, A2 to a parallelly-arranged position, and will reach a maximal value when the rotational arm RA has arrived at the horizontal position. For this purpose, a mechanism is provided that can increase or decrease a tensioning force provided by spring SP, and can act on the length of tensioning of spring SP, depending on a position of rotational arm RA relative to support column SC, or relative to a gravitational direction. The mechanism is referred to as angle compensation mechanism ACM that is schematically illustrated in FIGS. 4C to 4E, and the position of rotational arm RA specifically shown to be horizontal in the right section of FIG. 4C.

In FIG. 4C, angle compensation mechanism ACM is shown as a simplified exemplary embodiment, for the situation where rotational arm RA is horizontal, i.e. perpendicular to the gravitational direction. Angle compensation mechanism ACM includes a rod or bar R0 that is attached with one end to movable holder SL30, and with the other end attached to a pivot point P11 that can be laterally displaced along an axis PEA by a linear guiding mechanism LG10 that is perpendicular to an axis PEA of extension of rotational arm RA. A guiding block or mechanism (not shown) can be arranged at movable holder SL30 and at pivot point P11 forming a vertical groove to maintain movable holder SL30, rod R0, and pivot point P11 with roller CC12 in axis with PEA, pivot point P11 being linearly guided by a guiding structure LG10, for example to parallelly-arranged walls, or for example a U-shaped device, in which a bolt, cylinder, or sliding device that is arranged at pivot point P11 can linearly slide along axis PEA. Linearly displaceable pivot point P11 that can move along axis PEA includes a roller CC12 having a cylindrical round outer surface CC12S, roller CC12 configured to rotate about pivot P11, and pivot P11, roller CC12 and rod R0 are guided linearly along axis PEA that is perpendicular to an axis of extension of rotational arm RA, for example by guiding structure LG10. Moreover, ACM further includes a cam disk CC10 that has a cam actuation surface CC10S that is in contact with round outer surface CC12S of roller CC12, by the spring bias force of spring SP. Cam actuation surface CC10S forming an eccentric surface relative to point P10, for providing the variable radius or distance to round outer surface CC12S of roller CC12. Cam disk CC10 is attached to pivot point P10 that coincides or corresponds to pivot point P1 of main rotational arm RA and support column SC, and is rotationally fixedly attached to support column SC, while the remaining elements of ACM will rotate or turn with rotational arm RA relative to cam disk CC10. Cam disk CC10 with cam actuation surface CC10S forms an at least partially variable radius R when measured relative to pivot point P10 in different angular directions, having the longest possible radius R1, an intermediate radius R2 that is smaller than R1 but longer than R3, and the short radius R3 for engaging with roller CC12. The axis that is formed by pivot point P10 is arranged along a location of longitudinal extension of rod R0, when seen form the side view. Both the elements of spring load mechanism SLM and angle compensation mechanism ACM turn with main rotational arm RA, but for cam disk CC10 that is fixedly attached to support column SC, or to another references frame in case there is no support column SC, for example a wall or mounting plate or other device.

In the position shown in FIG. 4C, cam disk CC10 has an angular position relative to rod R0 and roller CC12 such that cam actuation surface CC10S is engaging with round outer surface CC12S of roller CC12 with a longest possible radius R1, in a position where rotational arm RA is horizontal. This signifies that rod R0 is not moving movable holder SL30 towards spring SP, and consequently attachment point P8.3 of spring SP is not moved to shorted spring SP. Therefore, spring SP will be tensioned to an original length DD1, being the longest extension that spring SP can take, providing for the strongest compensation force to linking mechanism LM, as required for a horizontal position of rotational arm RA, as shown in FIGS. 6A, 6B Next, as shown in FIG. 4D, rotational arm RA has been turned by 90° and is now vertical, as shown in FIG. 3B. This has caused rod R0, roller CC12, and the spring load mechanism SLM to turn or rotate relative to cam disk CC10 by 90°, as cam disk is fixedly installed to support column SC. During the turning by 90°, cam actuation surface CC10S has slid relative to round outer surface CC12S of roller CC12, or round outer surface CC12S of roller CC12 has rotated by the relative turning of cam actuation surface CC10S, so that cam actuation surface CC10S is engaging with round outer surface CC12S of roller CC12 at a shorter radius R3, thereby being progressively reduced with intermediate radii R2 during the turning. This shortening of radius R from R1 to R3 moves rod R0 towards a location of spring SP, and in turn moves moving movable holder SL30 and attachment point P8.3 of spring SP to reduce a tensioned length of spring SP, aided by the force provided by expanded spring SP, to thereby release energy from spring SP. By virtue of spring SP having been shortened from maximal distance DD1 to DD3, spring SP has less or no energy to act on transversal bar SL 20 via tilting bar SL10.

FIG. 4E shows a perspective and exemplary view of an embodiment of spring load mechanism SLM together with angle compensation mechanism ACM integrated to apparatus 100, where it can be seen that transversal bar SL20 is attached to linking mechanism LM having the form of a rod, while cam disk CC10 is fixedly attached via an opening in the back wall of rotational arm RA to support column SC, via a cylinder, having a rotational or center axis that coincides with first pivot P1. For accommodating angle compensation mechanism ACM, rotational arm RA can have a lateral arm member LAM. Main rotational arm RA is shown to be perpendicular to support column SC, but spring SP and is partially de-tensioned as tilting bar SL10 and spring SP are tilted off axis PEA, which means that arms A1 and A2 are not vertically arranged. Upon turning or rotational arm RA relative to support column, round outer surface CC12S of roller CC12 is urged against cam actuation surface CC10S at different locations having progressively changing radius R. Pivot axis P11 is linearly suspended by linear guiding mechanism LG10, that allows to displace rod R0 and movable holder SL30, to reposition attachment point P8.3 of spring SP.

In a variant, it is possible to implement angle compensation mechanism ACM with a cam disk CC10 and having a belt or chain attached thereto, instead of using a rod R0 and roller CC12. Chain or belt could pull attachment point P8.3 of spring SP as a function of the position of main rotational arm RA, by eccentric cam actuation surface CC10S engaging with a portion of Chain or belt to pull down attachment point P8.3 of spring SP.

FIG. 4F and FIG. 4G show different graphs that represent the torques and forces that are applied to first and second arm A1 and A2, as a function of a relative angular position of arms A1, A2 to main rotation arm RA, assuming that main rotational arm RA lies horizontally, with and without the compensatory effects of spring load mechanism SLM. For example, the graph of FIG. 4F shows an upper curve of a first torque that is caused by the weights to the assemblies of first and second arm A1, A2 as a function of an angular position of a longitudinal extension of the first and second arm A1, A2 relative to a direction of the gravitational force, in other words relative to a vertical position, within an angular range between 0° and ±28°, in the exemplary situation where PEA is parallel to a direction of the gravitational force, for example main rotational arm RA is horizontally arranged. Next, a middle curve is shown of a second torque that is caused by spring SP of spring load mechanism SLM that is acting on linking mechanism LM to first and second arms A1, A2, also referred to as the counter torque, designed to compensate the gravitation forces acting on the assemblies of first and second arm A1, A2. A third, lower curve is shown, being a resulting differential torque as a difference between the first torque and the second torque, being the torque that is applied to rotational arm RA with spring load mechanism SLM, as a function of the angle of first and second arm A1, A2. It can be seen that the differential torque is small and never exceeds 3 Nm, while the differential torque is zero when the arms A1, A2 extend in a direction of gravity, being 0°. Even at the maximal value of the differential torque is reached t about 17°, the frictional forces of all rotations of pivot points are not overcome, such that the position of arms A1, A2 around 17° remains stable.

Next, FIG. 4G shows a graph of different forces, for example a linearly rising curve showing a force that needs to be applied by a user or operator of the radiation apparatus or system to arms A1, A2 to maintain them at their position, as a function of their angle relative to main rotational arm. At angle 0°, a position of the arms A1, A2 is stable, and with an increasing angle, a force needed linearly increases, up to 14 kg or 140 N at the angle 28°. Next, a tolerable holding force is shown as a threshold value, being about 5 kg or 50 N. Thereafter, the holding force is shown after spring SP of spring load mechanism SLM has compensated the torques of arms A1, A2. It can be seen that a maximal holding force needed, again around the orientation angle 17°, is less than 1 kg or 10 N, and may not be strong enough to overcome the frictional forces of all the bearings of the pivot points. In other words, at any possible angular position, arms A1, A2 are stable as a result of spring load mechanism SLM.

Figure 5A:
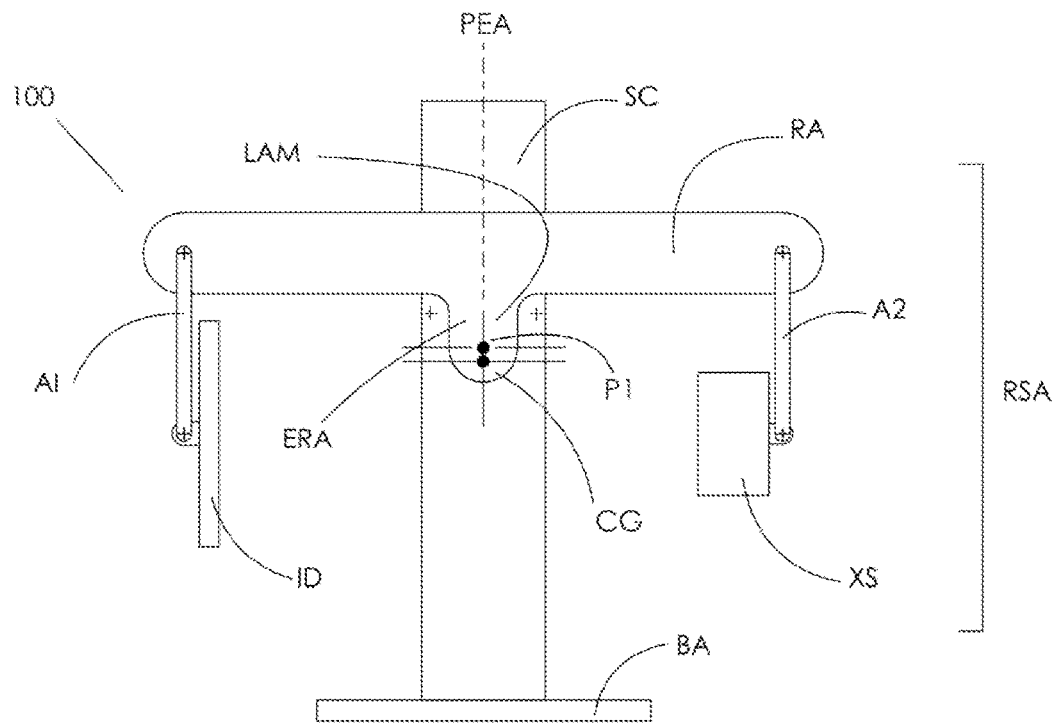
FIGS. 5A and 5B show another aspect of the present invention with respect to a center of gravity CG of the rotatable subassembly RSA including main rotational arm RA having a lateral arm member LAM, first and second arm A1, A2, imaging device ID, and radiation apparatus XS, wherein rotatable subassembly is designed such that center of gravity CG of the rotatable assembly lies at a distance away from first pivot P1 such that a torque that is caused by the rotatable assembly around the first pivot P1 counteracts to tension provided by spring SP of the spring load mechanism SLM when main rotatable arm RA is rotated from a vertical position to a horizontal position via angle compensation mechanism AMC, with FIG. 5A showing main rotatable arm RA in a horizontal position and thereby no torque is established by the offset of CG, and FIG. 5B showing main rotatable arm RA off the horizontal position so that torque will act to be compensated by force or tension provided by spring SP.
Figure 5B:
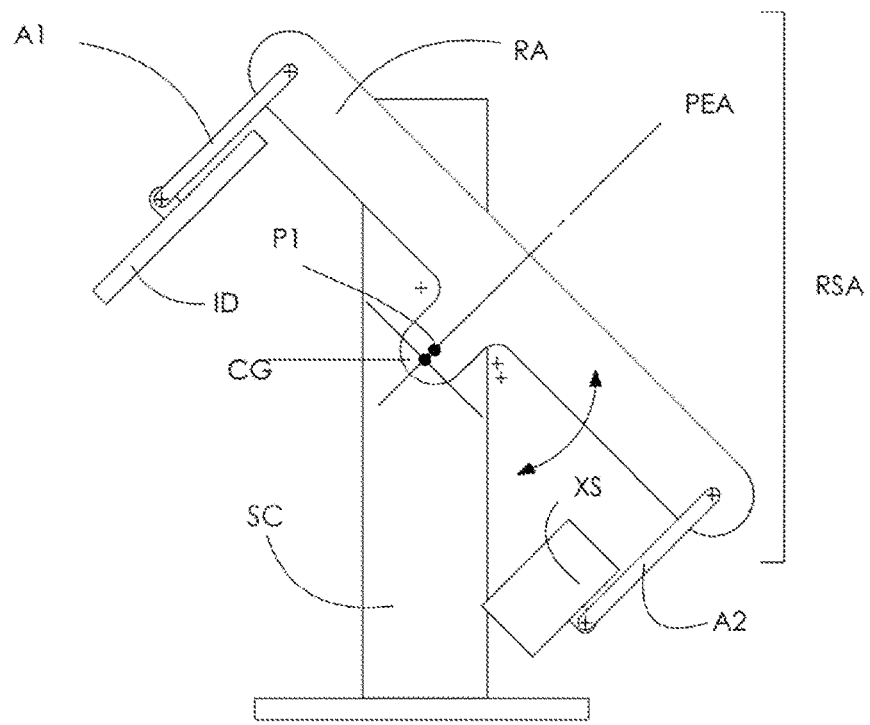

FIGS. 5A and 5B show another aspect of the present invention, where an exemplary and simplified side view is shown, in which a center of gravity CG of the rotatable subassembly RSA has a specific location relative to the axis of rotation or first pivot point P1, rotatable subassembly RSA including main rotational arm RA having a lateral arm member LAM, first and second arm A1, A2, imaging device ID, and radiation apparatus XS. Specifically, rotatable subassembly RSA is designed such that a center of gravity CG thereof lies at a distance or offset away from first pivot P1 such that a torque that is caused by the rotatable assembly RSA around the first pivot P1, resulting from the weight distribution of rotational subassembly RSA, counteracts to tension provided by spring SP of spring load mechanism SLM when main rotatable arm RA is rotated from a vertical position to a horizontal position via angle compensation mechanism AMC. Because the above-described angle compensation mechanism ACM detentions spring SP to a distance DD3 when rotational arm RA is vertically arranged, such that spring SP has no or little effect on linking mechanism LM, whilst spring SP is more tensioned when rotational arm RA is horizontally arranged, there is a certain torque or force required to be applied to rotational arm RA when it is turned from a vertical position to a horizontal position, to provide for kinetic energy to spring SP for its tensioning, for example to a position of spring SP having the longest possible distance DD1 to store the energy.

Without any other arrangement, this torque or force needs to be manually provided by user, operator, or radiographer to rotational arm RA, and can also cause rotational arm RA to be instable when in a horizontal position, to urge from an unstable horizontal position towards the mechanically stable vertical position, by the pulling exerted by spring SP via angle compensation mechanism ACM. For this purpose, as exemplarily shown in FIG. 5A, center of gravity CG is offset relative to first pivot P1, such that center of gravity CG of RSA is arranged spaced apart from pivot point P1 in a direction of extension of arms A1, A2, for example arranged along the direction of axis PEA, but can also be laterally slightly offset from axis PEA. Assuming rotational arm RA is horizontally arranged, center of gravity CG can lie below first pivot P1. Thereby, a torque is established by the offset of center of gravity CG relative to pivot point P1 that can at least partially compensate for a torque that is caused by the contracting spring SP of angle compensation mechanism ACM. FIG. 5B showing main rotatable arm RA off the horizontal position so that torque caused by the offset of center of gravity relative to pivot point P1 will act to be compensated by force or tension provided by spring SP, to provide for an equilibrium of rotational subassembly RSA. The placement of center of gravity CG at this location can for example be done by using arms A1, A2 of a certain length to move center of gravity CG to a desired position, using equipment having a requisite weight, for example for ID and XS, or by adding additional weights, or other means.

The mechanisms described with FIG. 2 with respect to linking mechanism LM, and spring load mechanism SLM and angle compensation mechanism ACM as described in FIGS. 4A-4E can be designed such that they are all located inside an enclosure that forms part of main rotatable arm RA, for example a rotatable arm RA that is formed as a hollow beam having a U-shape cross-section, that can be closed by a lid, for example a sealing lid for protection from for example but not limited to dust, humidity, particles. The lid can be welded to the hollow beam for making the enclosure somewhat permanent. In light of the low rotational speeds that are applied to the elements of mechanisms LM, SLM, and ACM, the hollow and closed rotational arm RA can be used for many years with no mechanical maintenance required, and at the same time providing very good protection from dust and other environmental conditions.

Figure 7B:
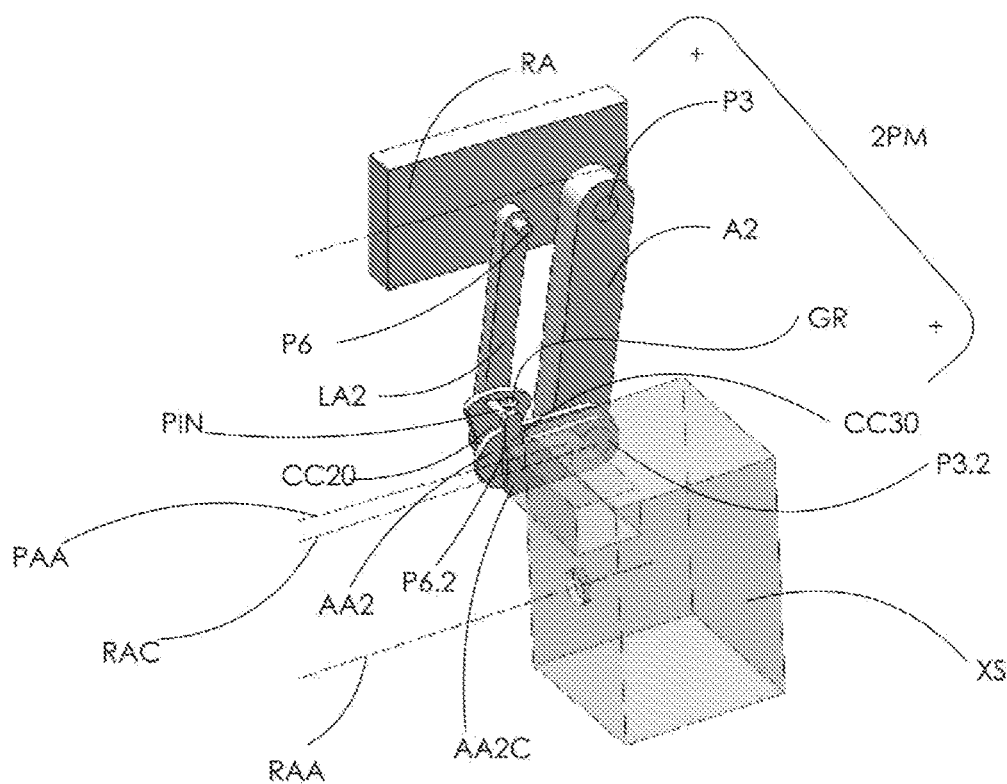
Figure 7C:
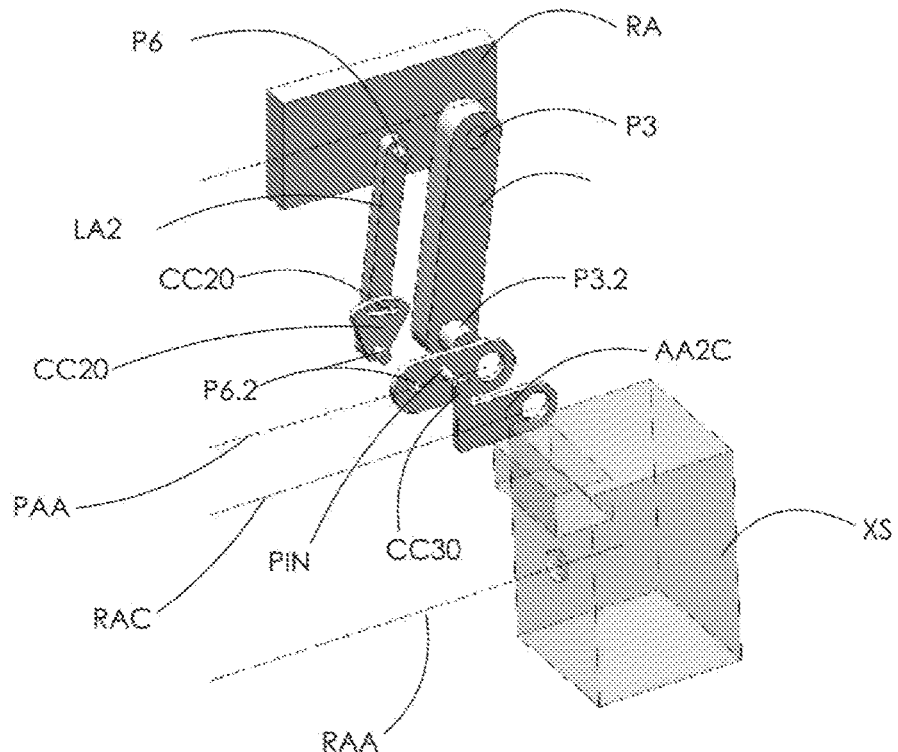
Figure 7D:
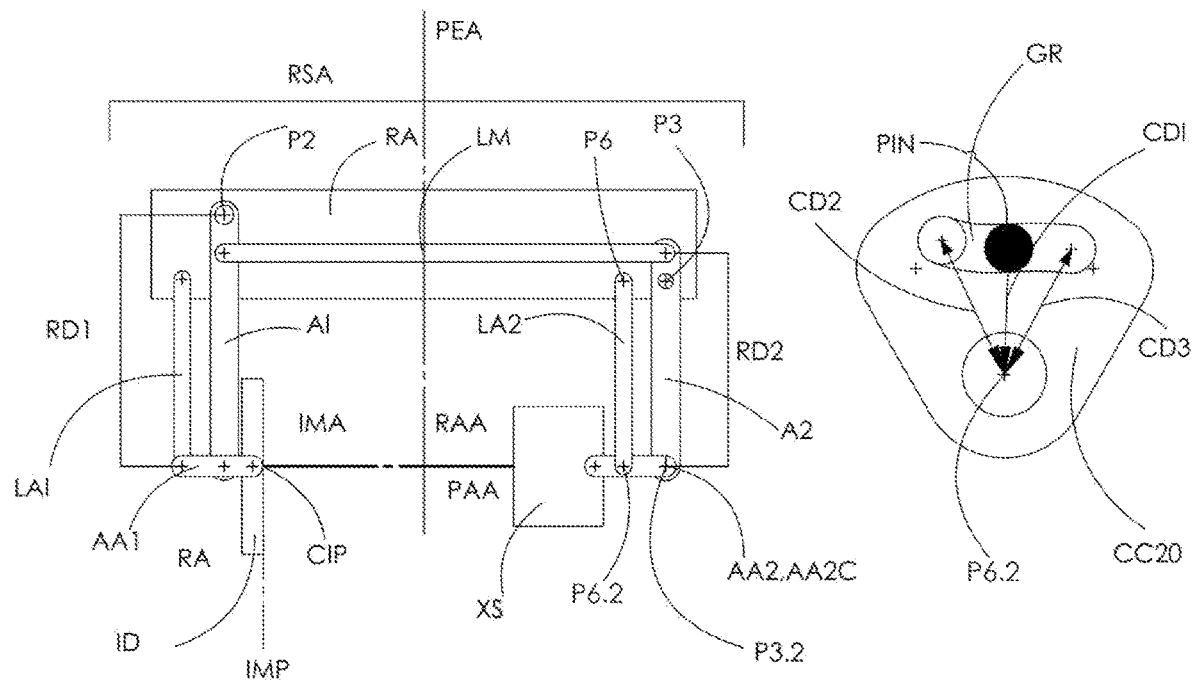
Figure 7E:
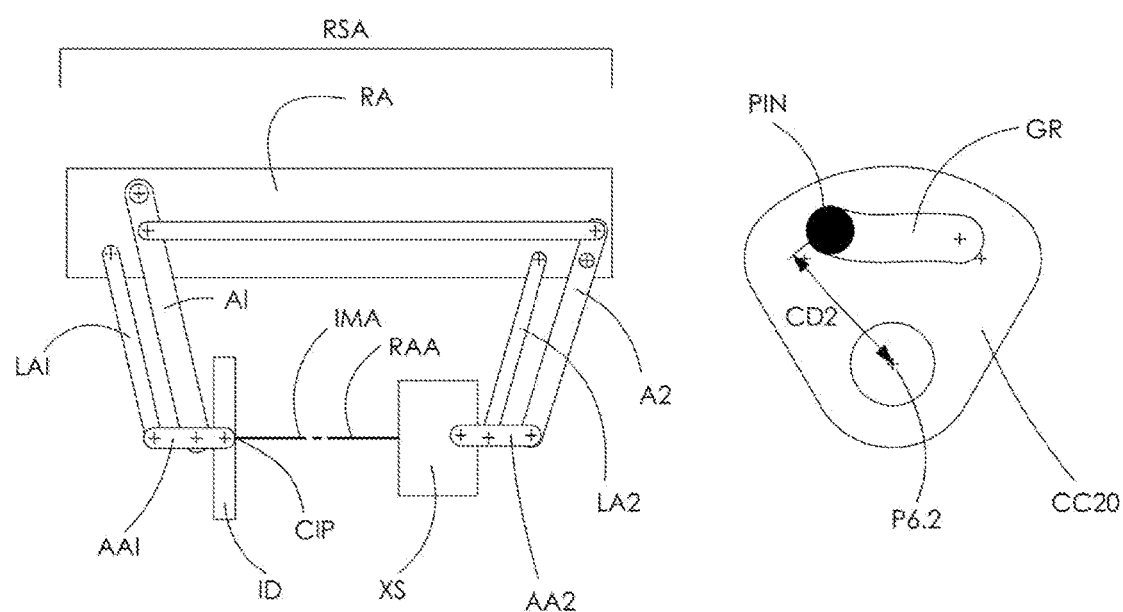
Figure 7F:
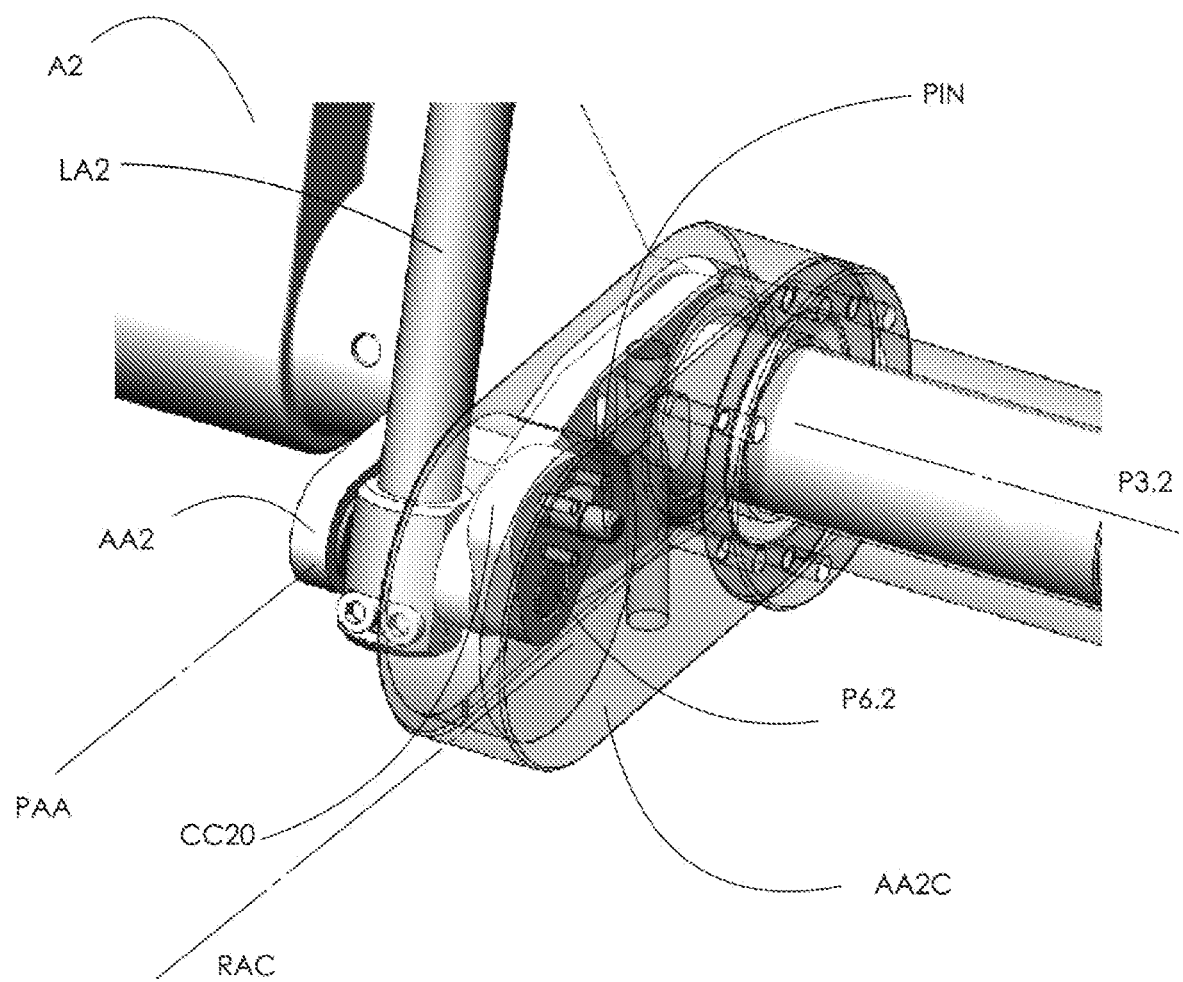

FIGS. 7A to 7F show an exemplary and simplified views illustrating another aspect of the present invention, where an angle between radiation axis RAA of radiation source XS and an linking arm axis PAA of second linking arm AA2 can be varied as a function of an angular position of second arm A2 relative to rotational arm RA. In the previous embodiments discussed herein, this angular relationship was fixed. For example, as illustrated in FIGS. 7D and 7E, an exemplary and simplified side view of a rotational subassembly SBA as a part of radiation apparatus 100 is shown, where and a first distance RD1 between an imaging axis IMA and pivot point P2 of first rotational arm A1 is different than a second distance RD2 between radiation axis RAA and pivot point P3 of second rotational arm A2. As a consequence, by having such arrangement, the imaging axis IMA and the radiation axis RAA will not always coincide with each other when the angular position of rotational arms A1, A2 relative to rotational arm RA is changed. Instead of preserving parallelism of IMA and RAA, it is also possible to ascertain that radiation axis RAA is substantially pointing towards a center of imaging plane IMP, irrespective of an angular position of first and second arms A1, A2. This requires that the radiation axis RAA of radiation source XS can change related to linking arm axis PAA of second transversal arm AA2, based on or as a function of an angular position of second arm A2 relative to main arm RA.

This can be done by using an additional radiation source holding arm AA2C, cam mechanism CC20, and pin mechanism CC30. For example, as shown in FIGS. 7A to 7C different views of the cam mechanism CC20, pin mechanism CC30, second parallelogram mechanism 2PM, and the additional radiation source holding arm AA2C, are provided. FIG. 7A shows an exemplary side view thereof, FIG. 7B shows a transparent top perspective view thereof, and FIG. 7C shows an exploded top perspective view thereof. The change of angle to radiation axis RAA relative to linking arm axis PAA can be done by a cam mechanism CC20 non-movably arranged with second linking arm LA2, cam mechanism CC20 embodied as a plate, block, tab, or element having a groove GR arranged therein, a longitudinal extension of groove GR arranged to be somewhat perpendicular to a longitudinal axis of extension of second linking arm LA2, such that cam mechanism CC20 turns with second linking arm LA2, and an additional radiation source holding arm AA2C that is arranged next to second traversal arm AA2, non-movably attached to a pin mechanism CC30, embodied as a plate, block, tab, or element with a pin or bolt PIN non-movably attached thereto. Pin PIN of pin mechanism CC30 is located and configured for a slidable and guiding engagement inside groove GR of cam mechanism CC20. Moreover, one end or part of second transversal arm AA2 is pivotably attached to second arm A2 with pivot P3.2, and one end or part of additional radiation source holding arm AA2C is also pivotably attached to second arm A2 with pivot P3.2. In other words, second traversal arm AA2, second arm A2, and radiation source holding arm AA2C can freely rotate towards each other around pivot P3.2, for example via a bolt or rod and bearings. An axis of extension of second transversal arm AA2 is defined as linking arm axis PAA, for example an axis that is defined as crossing pivot axes P3.2 and P6.2, while an axis of extension of additional radiation source holding arm AA2C is defined as holding arm axis RAC. However, unlike second transversal arm AA2, another end or part of additional radiation source holding arm AA2C is not pivotably arranged with pivot point P6.2, but has a pin or bolt PIN that is engaging with groove GR to force an angular position of holding arm axis RAC of additional radiation source holding arm AA2C relative to linking arm axis PAA of second transversal arm AA2.

This pivotable arrangement of additional radiation source holding arm AA2C around pivot point P6.2 that is guided or defined by pin PIN slidably engaging with groove GR can vary an angle between axis of orientation of linking arm axis PAA of second transversal arm AA2 and holding arm axis RAC of additional radiation source holding arm AA2C, when radiation source XS is approached or distanced from imaging device ID, which in turn means when an angle between second arm A2 and main rotational arm RA is changed. As radiation source XS can be non-movably attached to radiation source holding arm AA2C, holding arm axis RAC and radiation axis RAA will have a fixed angle relative to one other, for example they can be arranged parallel to each other, as exemplarily shown in FIG. 7A with a side view. Other orientation angles between RAC and RAA are also possible.

For example, in the situation shown in FIG. 7D, where second arm A2 and second linking arm LA2 are arranged to be perpendicular to main arm RA in the representation of rotational subassembly RSA shown on the left side, pin PIN is located substantially in the center of groove GR, so that a distance CD1 between pivot point P6.2 and a center axis of pin PIN is the shortest possible. In this position, a direction of holding arm axis RAC and a direction of linking arm axis PAA can be such that they substantially coincide, which means that RAC and PAA can be arranged to be parallel to each other. More importantly, in this position, radiation axis RAA of radiation source XS that is non-movably attached to additional radiation source holding arm AA2C can be arranged that it is parallel and coinciding with imaging axis IMA or with a center of imaging plane of imaging device ID.

In turn, in the situation shown in FIG. 7E, where second arm A2 and second linking arm LA2 are arranged to have an angle around 75° relative to main arm RA in the representation of rotational subassembly RSA shown on the left side, with the SID distance being shortened, pin PIN is located substantially at one end of groove GR, so that a distance CD2 between pivot point P6.2 and a center axis of pin PIN is longer as compared to distance CD1 represented in FIG. 7D. This change in distance ΔD from shortest possible CD1 to a longer CD2 as shown between FIGS. 7D and 7E will cause a slight rotation of additional radiation source holding arm AA2C around pivot point P3.2 relative to second transversal arm AA2, to thereby changing an angle between holding arm axis RAC and linking arm axis PAA, and by virtue of the non-movable attachment of radiation source XS to additional radiation source holding arm AA2C, for example, it can be configured to increase an angle of radiation axis RAA relative to linking arm axis PAA.

This change in angle between RAA and RAC relative to PAA allows to compensate for the fact that first arm A1 rotates around pivot point P2, having a radius length RD1 that is longer than second arm A2 that rotates around pivot point P3, having a radius length RD2. The result of the parallelogram mechanisms with first and second arms A1, A2, and the shorter arm radius lengths RD2 of second arm A2 as compared to RD1 leads to the fact that radiation axis RAA will not point to a center CIP of imaging plane IMP anymore, but somewhere spaced apart above the center, while still preserving parallelism between imaging axis IMA and radiation axis RAA. For example, with the position of first and second arms A1 and A2 as shown in FIG. 7E, a motion or displacement of a center point of imaging plane or axis IMA of imaging device ID relative to radiation arm in a direction PEA, in other words a direction that is perpendicular to an axis of extension of radiation arm RA, is larger than motion or displacement of a center point of radiation axis RAA of radiation source XS relative to radiation arm in a direction PUA, axes RAA and IMA would not coincide anymore. With groove GR that is shaped to change a distance CD1, CD2, CD3 relative to pivot axis P6.2, an orientation of axis RAA, RAC can be changed related to PAA. As shown in FIG. 7E, distance CD2 is longer to pivot point P6.2 as compared to the neutral position of pin PIN at distance CD1 presented in FIG. 7D so that axis RAC and RAA point slightly downwardly relative to axis PAA. Analogously, distance CD3 is longer to pivot point P6.2 as compared to the neutral position of pin PIN at distance CD1 presented in FIG. 7D so that axis RAC and RAA point slightly downwardly relative to axis PAA.

Would groove GR form a circular arc around pivot point P6.2, the distances CD1, CD2, and CD3 would not be varied, and thereby an angle between PAA and RAC would not vary irrespective of a position of pin PIN inside groove GR, as imitating a rotation of arm AA2C around pivot axis P6.2. However, a traversal extension of groove and their distances from pivot axis P6.2 can be chosen to provide for a different angular orientation of orientation axis RAC relative to orientation axis PAA, depending on an angle of orientation of arm A2 relative to main rotational arm RA, by having a groove GR that is non-circular or non-arcuate, as shown in FIGS. 7D and 7E.

FIG. 7C shows a top perspective and transparent view of a three-dimensional representation of cam mechanism CM20 with groove GR non-movably attached to second linking arm LA2, and pin PIN that is non movably attached to radiation source holding arm AA2C that is forming an enclosure, that depicts the situation of FIG. 7B where pin PIN is located at end section of groove GR, such the pin PIN has a distance CD2 to pivot axis P6.2 In a variant, cam mechanism CM20 with groove GR, pin mechanism CC30 with pin PIN, and the provision of an additional arm AA2C next to linking arm AA2 can be done at different pivot points or different arms. For example, it is possible that the roles of pivot points P6.2 and P3.2 are inversed, such that additional arm AA2C rotates around pivot point P6.2, and cam mechanism is non-movably attached to second arm A2. Also, as another example, cam mechanism CM20 with groove GR, pin mechanism CC30 with pin PIN can be operatively arranged at the first rotational assembly, for example to linking arm LA1 or first arm A1, to make sure that center location CIP of an imaging plane IMP coincides with radiation axis RAA.

In a variant, instead of using cam mechanism CC20 and pin mechanism CC30, also referred to as a cam and pin mechanism, to move the orientation of radiation source XS relative to linking arm AA2, that provides for a purely mechanical means for this angular change, it would also be possible to attach additional radiation source holding arm AA2C or radiation source XS to linking arm AA2 with a electro-mechanical means, for example a stepper motor, or other active device for changing the angular orientation between linking arm AA2 and radiation axis RAA. A position given by stepper motor could be controlled based on a measurement of a position of second arm A2 relative to main rotational arm RA, for example but not limited to by a rotary encoder that is operatively attached to one or more of the pivot points P3, P3.1, P3.2, P6, P6.2, by measuring a distance between second linking arm LA2 and second arm A2, or by measuring a distance between main rotational arm RA and transversal arm AA1.

Figure 8A:
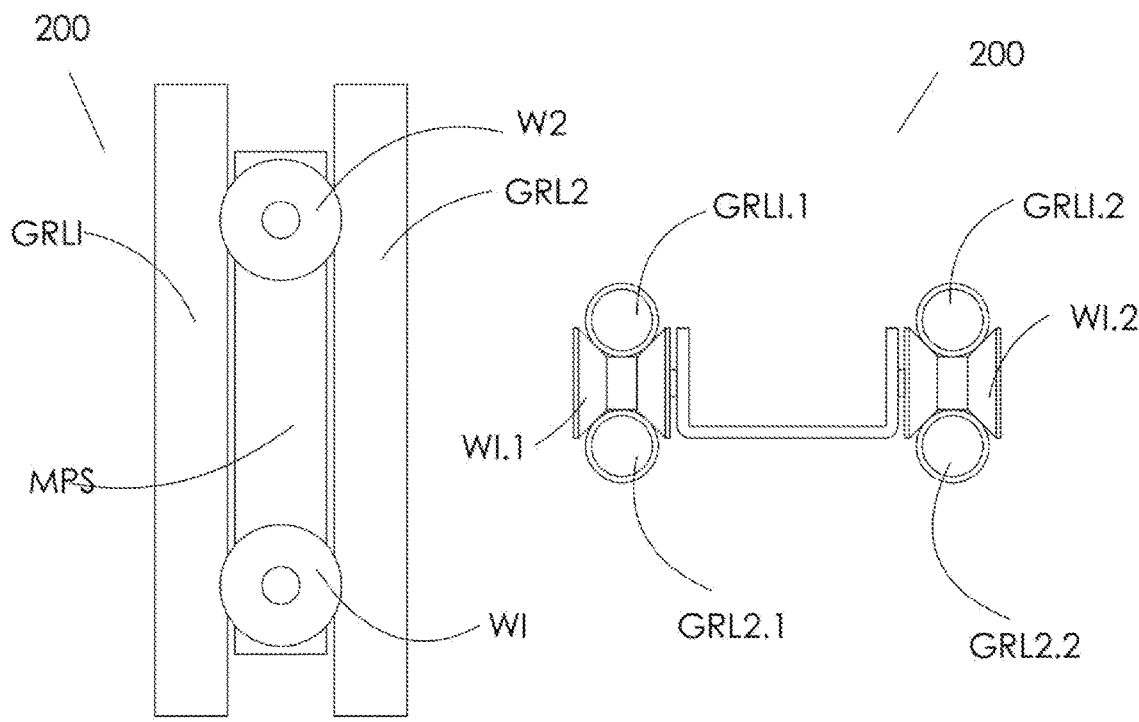
FIGS. 8A and 8B showing still another aspect of the invention, showing a linear guiding structure 200 for a support column SC of a radiation apparatus 100, to provide for a linear sliding mechanism of an arm, for example rotational subassembly RSA having main rotational arm RA, rotational subassembly RSA configured to slide up and down along a vertical extension of support column SC, linear guiding structure 200 including a first guiding rail GRL1, a second guiding rail GRL2 arranged in parallel to first guiding rail GRL1, a first wheel W1 in contact with first guiding rail GRL1, and a second wheel W2 in contact with second guiding rail GRL2, arranged at a distance from the first wheel W1, the first and second wheels rotatably attached to a mounting part MPS, mounting part MPS operably and rotationally attached to main rotational arm RA of the rotational subassembly RSA, first guiding rail GRL1 arranged substantially in parallel to a longitudinal extension of support column SC, first guiding rail GRL1 arranged to be closer to a vertical opening VO as compared to the second guiding rail, and rotational subassembly RSA is attached to linear guiding structure 100 such that the first wheel W1 is urged against the first guiding rail GRL1, and second wheel W2 is urged against second guiding rail GRL2 by a torque caused by a weight of rotational subassembly RSA.
Figures 8B, 8C:
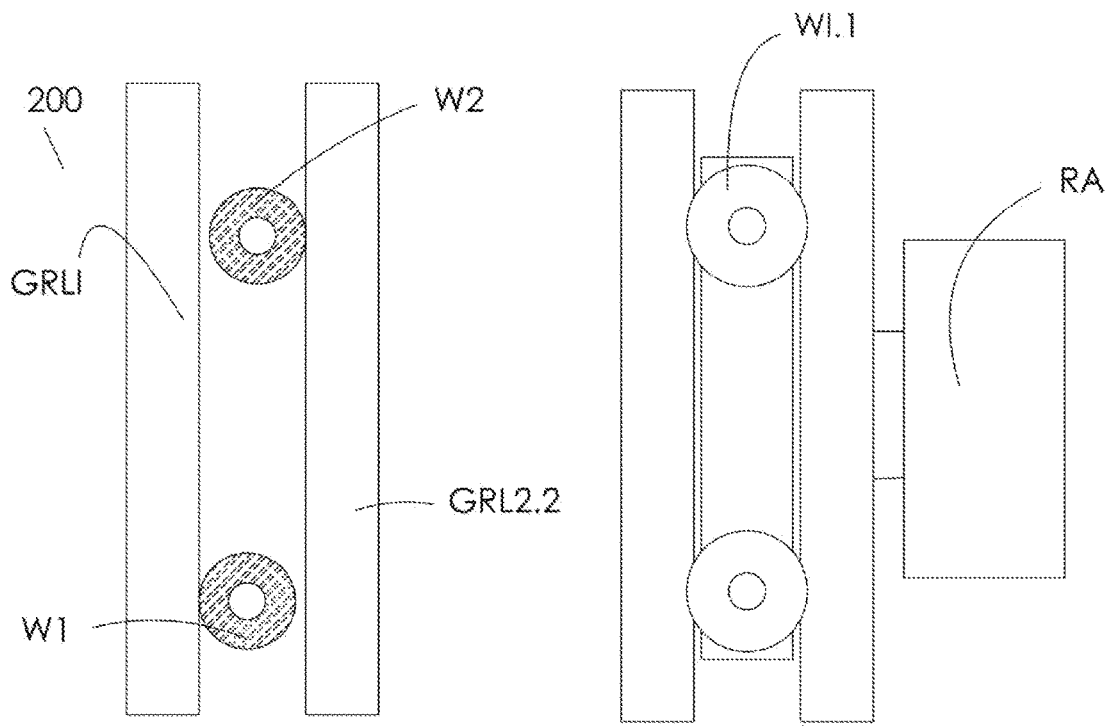

According to another aspect of the present invention, a linear guiding structure 200 is provided for movably suspending a rotational subassembly RSA to a support column SC or wall, or other mounting device, as exemplarily and schematically shown in FIGS. 8A and 8B. FIG. 8A shows on the left side a side view in a direction of rotational axis of wheel assemblies W1, W2, and shows on the right side a top view in a direction of an axis of extension of support column SC or guiding rails GRL1, GRL2, or in a direction of the linear motion, and FIG. 8B shows another side view, depicting slider SLI forming a mounting part for both main rotational arm RA and wheel assemblies, with upper wheel assembly W2 that include two wheels W1.1 and W1.2, and a lower wheel assembly W1 that includes two wheels W2.1 and W2.2, wheels W1.1 and W2.1 mounted to one side of slider SLI, and wheels W1.2 and W2.2 mounted to the other side of slider SLI. Linear guiding structure 200 also includes a first and second guiding rail pairs GRL1, GRL2, all four (4) guiding rails GRL1.1, GRL1.2, GRL2.1, and GRL2.2 arranged in parallel to each other, and also being substantially in parallel with a vertical extension of support columns SC. GRL1, 2 can be embodied as rails, tubes, poles, bars, or other longitudinally-extending mechanical elements on which wheels can roll.

As shown in FIG. 8B that shows a side view, a distance between a RSA assembly facing rails GRLS2, and the rails GRL1 located away from rotational subassembly RSA wheels W2.1 and W2.2 of upper wheel assembly W2 are such that upper wheels W2 will be in rotatable touch with RSA assembly facing rails GRLS2, while lower wheels W1 will be in rotatable touch with rails GRL1 located away from rotational subassembly RSA. A gap is provided between wheels W2.1, W2.2 of upper wheel assembly W2 and rails GRL1, and between wheels W1.1, W1.2 of lower wheel assembly W1. Rotational subassembly RSA is rotatably attached by first pivot P1 to slider SLI of linear guiding structure 200 on the right side as shown in FIG. 8B, such that wheels W1.1, W1.2 of lower wheel assembly W1 are urged against the first guiding rail GRL1, and heels W2.1, W2.2 of upper wheel assembly W2 are urged against second guiding rails GRL2, by virtue of a torque caused by a weight of rotational subassembly RSA. This arrangement allows to provide for a mechanically simple and durable linear motion structure to move slider SLI with rotational subassembly RSA up and down support column SC, or other type of mounting device, having relatively large dimensions that allow for easy cleaning with little sensitivity to dust and debris deposit.

Figure 9B:
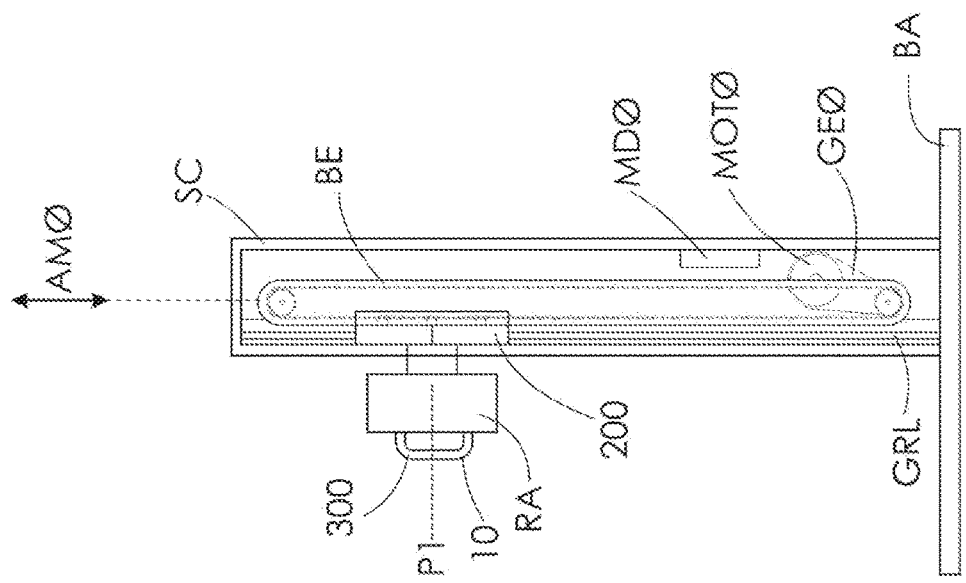
FIGS. 9A and 9B show an exemplary and simplified frontal view and side view of a radiation apparatus 100 that can have different motor-assisted arms RA, A1, A2, AA1, AA2, for aiding movements or displacements of the arms RA, A1, A2, AA1, AA2, for example a motor-assisted movement of main rotational arm RA along a linear axis of motion AM0 relative to support column SC to move arm RA up and down, assisted by motor MOT0, and/or other types of motor assistance or actuation, and different exemplary positions of a handle 300 that is configured to measure an effort provided by user.
Figure 9A:
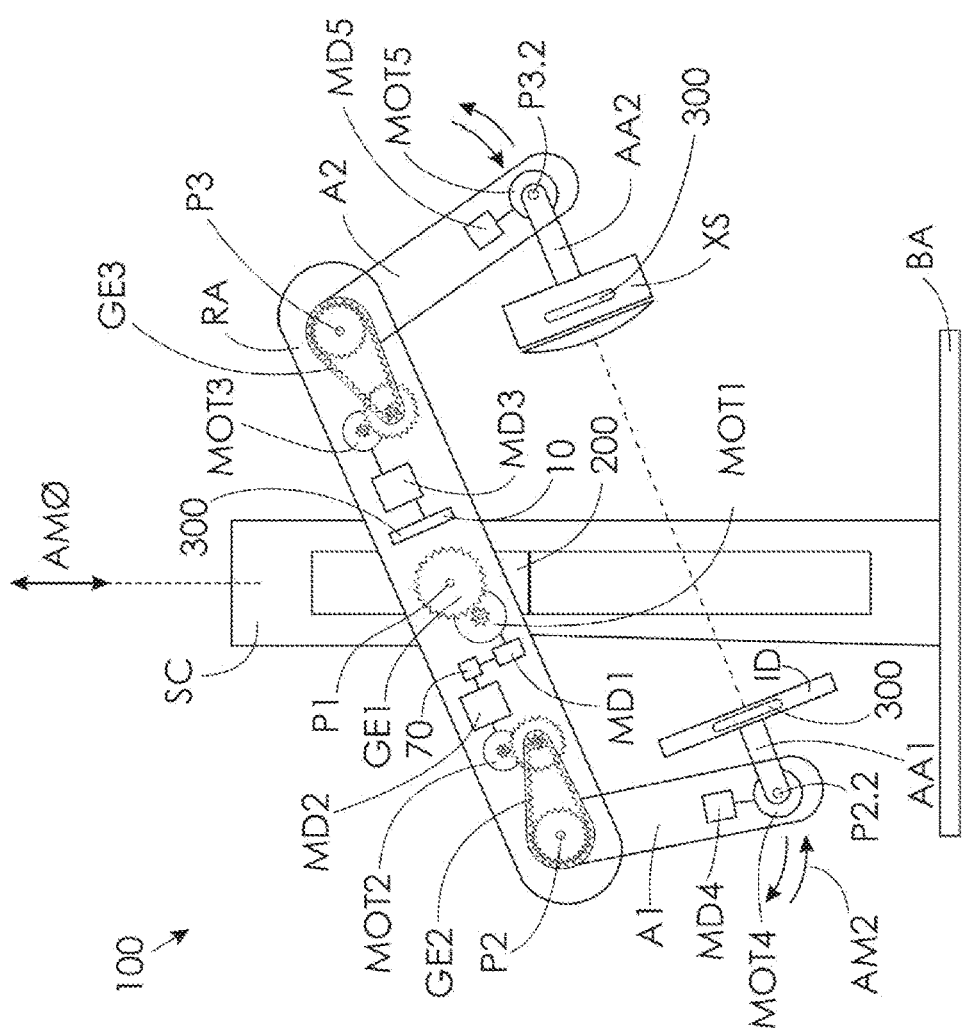

FIGS. 9A and 9B show an exemplary and simplified frontal view and side view of a radiation apparatus 100 that can have different motor-assisted arms RA, A1, A2, AA1, AA2, for aiding movements or displacements of the arms RA, A1, A2, AA1, AA2, for example a motor-assisted movement of main rotational arm RA along a linear axis of motion AM0 relative to support column SC to move arm RA up and down, assisted by motor MOT0. For simplification purposes, FIG. 9B depicts a cross-sectional view to see a simplified version of the interior of support column SC, and with main rotational arm RA arranged in a horizontal position. Also, FIG. 9A shows a handle 300 that can be placed at different positions of radiation apparatus, handle 300 configured to measure an effort by user to move or otherwise displace at least one of the arms of radiation apparatus 100, as further discussed below. Other examples of motor-assistance of elements of radiation apparatus that are presented in FIGS. 9A and 9B can be the motor assistance of a rotation of main rotational arm RA around pivot axis P1 relative to support column SC, with assistance of motor MOT1, motor assistance of a rotation of arm A1 holding imaging device ID relative to main rotational arm RA around pivot axis P2 with motor MOT2, a motor assistance of a rotation of arm A2 holding radiation source XS relative to main rotational arm RA around pivot axis P3 with motor MOT3, for example when varying a source-image distance SID between imaging device ID and radiation source XS, motor assistance of a rotation of imaging device ID holding arm AA1 around pivot axis P2.2 relative to arm A1 with a motor MOT4, for example for adjusting an imaging angle relative to radiation source XS, and a motor assistance of a rotation of radiation source XS holding arm AA2 around pivot axis P3.2 relative to arm A2 with a motor MOT5, for example for adjusting a radiation angle relative to imaging device ID.

In this respect, FIGS. 9A and 9B also show a motorized embodiment and variant of radiation apparatus 100, where linking means can be implemented by a first motor MOT1 that operatively acts on first arm A1, to rotate arm A1 around pivot point P2, and a second motor MOT2 that operatively acts on second arm A2, to rotate arm A2 around pivot point P3, instead of the use of a purely mechanical linking mechanism LM. As explained above, these two motors MOT1, MOT2 can be configured to directly act on the axes that form pivot points P1, P2, or via a gearing, belt drive, chain, rack and pinion using linear motors, sprockets, or other mechanical interconnection GE1, GE2 to provide for the rotation of arms A1, A2. Motors MOT1, MOT2 can include a stepper or stepping motor, for example having a low rotation resistance when they are not powered, and can further include the corresponding motor driver circuits MD1, MD2, for example an inverter for a brushless-type motor. Moreover, motors MOT1, MOT2 can include or be otherwise equipped with a rotational position sensor or position tracking sensor RP1, RP2, for example a rotary or shaft encoder, or can also be operator in an open-loop angular position control, without angular feedback by a separate sensor. Motors MOT1, MOT2 can be controlled and operated by a controller, data processor, or computational device 70, and the rotational position sensors RP1, RP2 can also be in operative connection with the controller 70, for example a microcontroller. For example, controller 70 can be configured to set an angular position of first arm A1 relative to main rotational arm RA with first motor MOT1, depending on a measured angular position of second arm A2 relative to main rotational arm, for example by measuring the angular position at motor MOT2 with a RP2. The angles of first and second arm A1, A2 can thereby be analogous to the angular positions that are mechanically provided by transversal bar of linking mechanism LM, such that a reduction or an increase of the SID distance. For example, a rotation of arm A1 by 15° could be measured or sensed from sensor RP1 with controller, and the controller could then instruct a rotation of arm A2 by −15° with motor MOT2. Motors MOT1, MOT2 could also be controlled to hold a certain angular position, and either arm A1 or arm A2, still able to be moved by a manual operation, or by instructions from controller 70. The correspondence of the angles of orientation for arms A1, A2 can be calculated, or can be based on a correspondence look-up table.

Moreover, in the motorized variant and embodiment, it is also possible that imaging device ID can turn relative to first arm A1 within an angular range around pivot point P2.2 with a motor MOT4, and that radiation source XS can turn relative to second arm A2 within an angular range around pivot point P3.2 with a motor MOT5, with the goal to preserve that radiation axis RAA points substantially to a middle CIP of imaging plane IMP, or with the goal to preserve that radiation axis RAA and imaging axis IMA coincide with each other. For this purpose, motor MOT4 can be arranged to rotate or turn imaging device ID relative to first arm A1, and motor MOT3 can be arranged to rotate or turn radiation source XS relative to second arm A2. Also, each motor MOT4, MOT5 or pivot point P2.2 and P3.2 can be equipped with a rotary position sensor RP3, RP4, respectively. Controller 70 can be configured to control motor MOT2 acting between arm A2 and arm RA, motor MOT4 acting between imaging device ID and arm A1, and motor MOT3 acting between radiation source XS and arm A2, to adjust their positions upon a manual motion to arm A1, and analogously, controller can be configured to control motor Ml acting between arm A1 and arm RA, motor MOT4 acting between imaging device ID and arm A1, and motor MOT3 acting between radiation source XS and arm A2, to adjust their positions upon a manual motion to arm A2. This allows a user to manually adjust a SID between imaging device ID and radiation source XS, for example by manually moving either arm A1 or arm A2, and at the same time, controller can controlling motors MOT4, MOT5 to make sure that radiation axis RAA and imaging axis IMA are arranged to coincide with each other irrespective of the SID distance, or that radiation axis RAA substantially points to a center CIP of imaging plane IMP of imaging device ID irrespective of the SID distance. For performing these motor control operations, controller 70 can be configured to use a PID controller scheme, based on measured angle from either arm A1 or A2, and three set angles for the different angular positions for either arm A2 or A1, and ID and XS, based on a correspondence table.

Also, FIGS. 9A and 9B show an exemplary placement of a handle 300 having a holding element 10 that allows a user to hold by a hand of a user to move arm RA to provide for a human force or torque, or both to move main rotational arm RA, and also includes one or more measurement devices 40, 50, as shown in the different views of FIG. 10, to measure the human force or torque, or both provided by user U via handle 300. Also, with respect to radiation apparatus 100 shown, the arm RA is exemplarily shown to be a one that can rotate around a pivot axis P1 in addition to the translational up and down displacement along axis AM0, but it is also possible that arm RA is only configured to move translationally along axis AM0 without the possibility to rotate around pivot axis P1. As shown in FIG. 9A, One or more handles 300 can be placed at different positions of radiation apparatus, for example on any of the movable elements of radiation apparatus 100, for example at main rotational arm RA, at imaging device ID, at radiation source XS, or at one of the arms AA1, AA2, one of the arms LA1, LA2, or a combination thereof.

The one or more measurement devices 40, 50 can be configured to generate signals that are representative of the effort of user U for moving rotational arm RA, for example a value indicative of the force or torque manually applied by the user, and these signals provided by handle 300 or another computing device that can be used for controlling motor MOT0 with motor driver MD0 for providing assistive motor support to move main rotational arm RA along linear axis AM0. In this way, the human effort by user U to move main rotational arm RA relative to support columns SC can be assisted, amplified, or enhanced by power from motor MOT0. Not shown in FIGS. 9A to 9B, handle 300 can also be placed on rotational arm A1, or on rotational arm A2, or on another moveable element of radiation apparatus 100, so that user U can engage and move handle 300 with the goal to move one of the arms A1, A2, RA of radiation apparatus RA, and provide for motor assistive support by motors MOT1, MOT2, and MOT3.

In the variant shown, handle 300 can be placed substantially in the middle of main rotational arm RA on the front facing surface, so that a user U can easily reach and hold onto holding element 10 of handle 300, for example with one hand, with the goal by user U to move rotational arm RA upwards and downwards along axis AM0, being the axis of vertical extension of central column SC. In another variant, handle 300 is affixed or otherwise arranged at the radiation source XS and/or the imaging device ID. As main rotational arm RA can have substantial weight, as it holds imaging device ID and radiation source XS, as well as arms A1 and A2 and possibly many other mechanical and electrical elements, the use of solely manual force to move main rotational arm RA can be quite burdensome and require a substantial force from user U. Therefore, a first user assist or force amplification function can be the assisting of this linear up- and down motion provided by handle 300 along axis AM0 with a motor MOT0 can be arranged at support column SC, to rotate a belt BE or chain with or without a gearing GE0 that allows to linearly move linear guiding structure 200 up and down. Instead of a rotational motor MOT0, for example a stepper motor, that acts via a gearing GE0 rotativity on a belt or chain BE, a linear motor could be used for MOT0, directly or indirectly linearly acting on linear guiding structure 200 in a direction of axis AM0. Linear guiding structure 200 can be one as described herein with FIGS. 8A to 8C, but can also be a different element that allow main rotational arm RA to move up and down support column SC. Handle 300 is configured to measure a signal or value that is representative of the effort of user U to move main rotational arm RA along axis AM0 relative to support column SC, and this signal or value can be used as a set value for motor driver MD0 to control a force of motor MOT0 that is provided to linear guiding structure 200 via gearing GE0 and belt BE.

As a second user assist or torque amplification function, handle 300 can be turned or rotated by user U with the goal to impart a rotation of main rotational arm RA around pivot axis P1, and motor MOT1 via gearing GE1 can provide for assistive or amplificative support torque to rotate main rotational arm RA around pivot axis P1. In this respect, handle 300 can be configured to measure a signal or value that is representative of the effort of user U to turn or rotate main rotational arm RA around axis P1 relative to support column SC, and this signal or value can be used as a set value for motor driver MD1 to control a torque of motor MOT1 that is provided to rotate main rotational arm RA via gearing GE1. Additional assist and torque amplification functions of radiation apparatus 100 are also possible, for example a motor assisted turning of arm A1 around pivot axis P2, with the motorized support by motor MOT2 and optionally gearing GE2, a motor assisted turning of arm A2 around pivot axis P3, with the motorized support by motor MOT3 and optionally gearing GE3. For the torque-assist of the rotation of arms A1, A2, a handle 300 can be used that is placed on arm A1 or A2 that allows to measure the torque provided by user U to arms A1, A2, or arms A1, A2 can be directly equipped with sensors that allow to measure a torque that a user applies to arms A1, A2, to thereby determine a signal or value that is indicative of the user-generated torque to add an assistive or amplified motor torque with motors MOT2, MOT3 via motor drivers MD2, MD3. Additional motor assistance can be provided by a rotation of imaging device ID holding arm AA1 around pivot axis P2.2 relative to arm A1 with a motor MOT4, for example for adjusting an imaging angle relative to radiation source XS, and a motor assistance of a rotation of radiation source XS holding arm AA2 around pivot axis P3.2 relative to arm A2 with a motor MOT5, for example for adjusting a radiation angle relative to imaging device ID, and a measurement of a user force or torque to move arms AA1 and AA2, for example by using signals indicative of a torque or force applied to arms AA1, AA2, respectively, for example measuring a strain on arms AA1, AA2, that has been manually applied, or by measuring a force or torque with a handle 300 that is attached to arms AA1, AA2.

Figure 11:
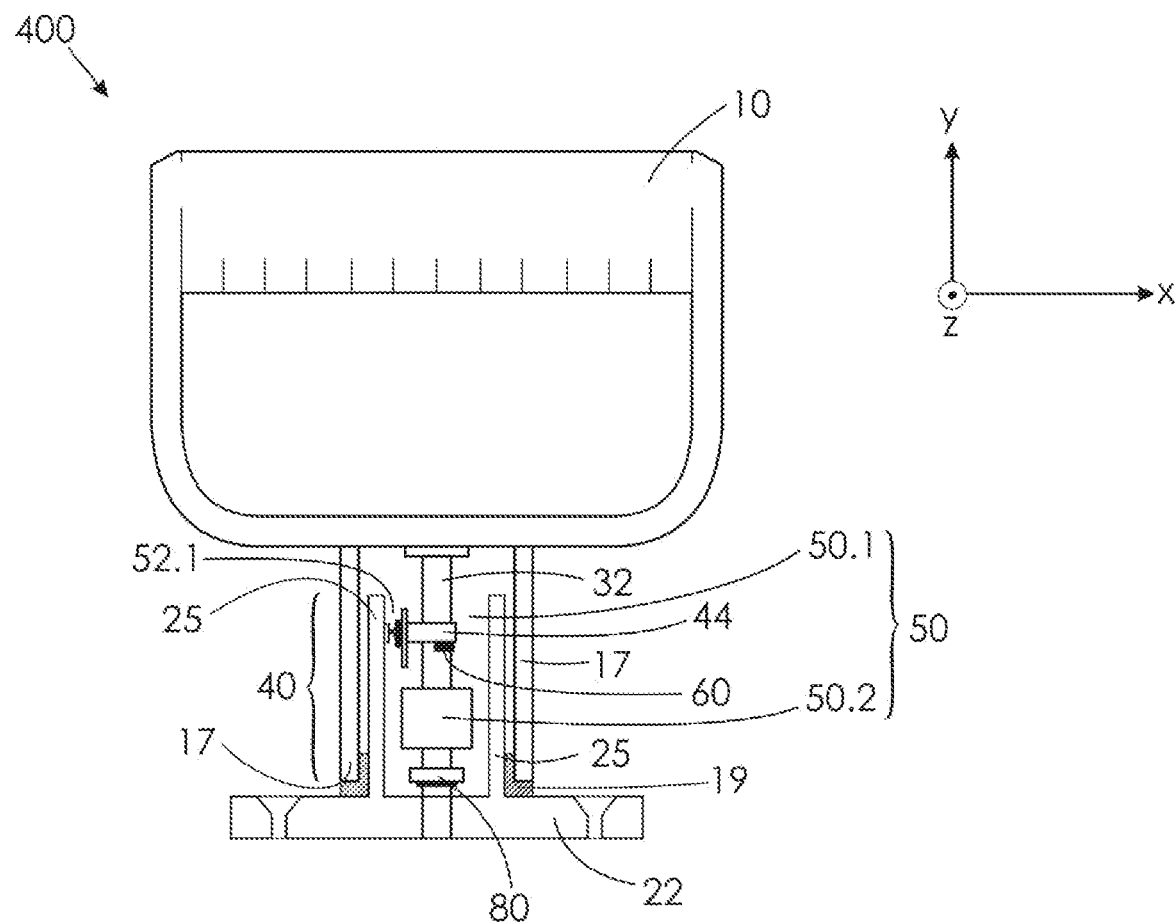
FIG. 11 shows a side view of another exemplary handle 300, having one (1) connection element 32.

With respect to handle 300 that can be attached to main rotational arm RA, and two exemplary embodiments thereof are shown in FIGS. 10 and 11, respectively. In the variant shown of FIG. 10, handle 300 includes a holding element 10 configured to be held by a hand of a user to move main rotational arm RA, the holding element 10 having a U-shape and having a handle part 15, a base member 20 that includes two separate elements 20.1 and 20.2 to attach to each end of the U-shaped holding element 10, each element 20.1 and 20.2 including a base elements 22, 24, respectively, configured to be attached to main rotational arm RA, and an interconnection member 30 including two interconnection elements 32, 34 that are formed as rods or bars, these two interconnection elements 32, 34 each interconnecting holding element 10 and one of the base elements 22, 24. At least a portion of interconnection elements 32, 34 is configured to bend or displace upon engagement of the user with the holding element 10, for example when user U pulls, pushes, turns, or otherwise manually applies a force or a torque to holding element 10 of handle 300, as the force or torque applied by user U will transmit from holding element 10 via interconnection elements 32, 34 to the respective base elements 22, 24 to rotational arm RA. Moreover, an upper section of interconnection element 32, 34 can be attached to holding element via a bolt, screw, or shaft 34, 36, respectively, and a corresponding bore or hole in a part of holding element 10, and this arrangement allows for a slight rotational movement between interconnection elements 32, 34. In a variant, base member 20, for example base elements 22, 24, but even inner elements 25.1 and 25.2 can be integrally formed with a wall of a rotational arm RA, or of another element of radiation apparatus 100, for example a side wall of imaging device ID or radiation source XS, or can be part of one of the movable elements RA, A1, A2, AA1, AA2, XS, ID, of radiation apparatus 100.

Moreover, handle 300 also includes a measurement unit 40 configured to measure a value indicative of an amplitude and direction of a force applied by the user to handle 300. For example, measurement unit 40 can include one or more sensors that can measure a signal that is indicative of a value of a pulling or pushing force or the user U, and a direction of the pulling or pushing force, for example a direction relative to axis of motion AM0. For example, measurement unit 40 can include a first measurement device 50 that can measure a bending or a displacing of one of the interconnection elements 32, 34, for example by a distance measurement sensor that measures a lateral flexing of the rods or bars that form the interconnection elements 32, 34, or by a strain gage sensor that can also measure a flexing applied to the rods or bars of interconnection elements 32, 34, for example by using strain gauge transducers in a Wheatstone bridge configuration. The distance measurement sensor can be based on different types of measurement principles, for example optical reflective triangulation, capacitive or inductive distance measurement, ultrasonic measurements, laser-based time-of-flight (TOF) measurements with pulsed-based or continuously modulated lasers.

In the variant shown of FIG. 10, first measurement device 50 includes a distance measurement sensor 52.1 that is attached to interconnection element 32, for example an optical distance measurement sensor, attached thereto with a clamp 54.1 or other element that can fixedly attach distance measurement sensor 52.1 to interconnection element 32, for example a fastener, bracket, brace, to measure a distance between interconnection element 32 and a wall 25.1 that is attached to first base 20.1. Upon bending of interconnection element 32 due to a manually-applied force, a distance measured by distance measurement sensor 52.1 will vary, and provide for a signal that is indicative of a force applied in the x-direction. Moreover, first measurement device 50 can further include a distance measurement sensor 52.2 is arranged at interconnection element 34, attached thereto with a clamp 54.2 or other element that can fixedly attach distance measurement sensor 52.2 to interconnection element 34, to measure a distance between interconnection element 34 and a wall 25.2 that is attached to second base 20.2. Upon bending of interconnection element 34 due to a manually-applied force, a distance measured by distance measurement sensor 52.2 can vary, and provide for a signal that is indicative of a force applied in the z-direction, the z-direction being substantially perpendicular to the z-direction. With this arrangement of first measurement device 50 having two different sensors 52.1 and 52.2 that are arranged to be rotated by 90° towards each other, two separate signals that are representative of a first in two different perpendicular directions along the x-direction and the z-direction can be measured, thereby measuring a force applied to a plane that is perpendicular to a rotational axis P1 of arm RA.

In addition, measurement unit 40 can further include a second measurement device 60 that can capture or measure an absolute orientation of handle 300 and therefore the absolute orientation of main rotational arm RS, as handle 300 and main rotational arm RA can take different rotational positions relative to support column SC, due to a rotation around pivot point P0. Second measurement device 60 can include an accelerometer, a magnetometer, or a gyroscope, or a combination thereof. For example, second measurement device 60 can include a inertial measurement unit (IMU). As an alternative, second measurement device 60 can be a sensor that detects a direction of the gravity, for example by use of piezo disk vibration technology, one or more mercury tilt sensor switch or other type of tilt switches, for example ones using liquid conductor switches for detecting a gravity-direction referenced orientation. In an exemplary embodiment, second measurement device 60 is attached to a base of interconnection element 32 of handle 300, but could also be attached to base 22 or any other part of handle 300, or can also be attached outside of handle 300, for example to rotational arm RA.

With such measurement unit 40 configured to measure a value that is indicative of the amplitude of the force applied by user U, and a value that is indicative of a current rotational position of main rotational arm RA relative to support column SC, it is possible to calculate an actual force FF that is being provided by user U that is in a direction of axis of motion AM0, and to determine whether user U is pulling rotational arm RA downwards or pushing rotational arm RA upwards. This can be done by a data processor 70 can receive signals and perform data processing from data, signals, or values from measurement unit 40, for example first and second measurement devices 50, 60, to output a value of the force in a direction along the axis of motion AM0. This data processor 70 can be located withing handle 300, but can also be located outside handle 300, for example inside or at main rotational arm RA. In a variant, second measurement device 60 can alternatively or additionally include a rotary encoder that is in operative connection with pivot axis P1 to determine a rotational position of main rotational arm RA relative to support column SC, and can provide data of the actual rotational position to data processor 70.

Holding element 10 can be embodied as different types of elements that allow a user to hold on to with one or more hands, to displace or otherwise move the motorized arm of a radiation apparatus 100, for example a handle, bar, rod, shaft, handgrip, knob, lever, gripping tool, hold. In the variant shown in FIG. 10, holding element 10 is formed as a U-shaped tubular structure with a thinned out middle section 16 for increasing a holding grip of a user, and two leg portions 12, 14 also being cylindrically shaped.

Base element 20 can be embodied as a rigid structure that allows to be fastened to or otherwise fixedly or removably attach to a portion of the motorized arm of the radiation device 100, preferably at a position where the holding element 10 can be easily grasped by the user. In the variant shown in FIG. 10, base element 20 is formed by two separate elements 22, 24 that have a substantially square-shaped bases 26, 28 with exemplary four (4) openings to allow an attachment of the respective base element 22, 24 with screws, rivets, bolts, snap-lock clips, adhesive, nails, and can also include an inner protective wall 25.1, 25.2, for example a cylindrical element 25.1, 25.2, that can have a circular or oval cross-sectional shape when viewed in a direction of the y-axis, that has a narrower diameter than an outer protective wall 17.1, 17.2, for example cylindrical elements 17.1 and 17.2 that forms the two leg portions 12, 14, such that inner cylindrical elements 25.1, 25.2 of base element 20 can be placed inside leg portions 12, 14, respectively. The overlap of outer cylindrical elements 17.1 and 17.2 and inner cylindrical elements 25.1, 25.2 along the y-direction provide for a protection of the electronics of the measurement device 40, and also a protection to the interconnection elements 32, 34. This allows to provide for a gap or spacing between holding element 10 and base element 20, to allow for the bending, flexing or other type of displacement of interconnection elements 32, 34 for the force or torque measurements. For sealing purposes, the space between outer cylindrical elements 17.1 and 17.2 and inner cylindrical elements 25.1, 25.2 can be filled with a sealant 19 (shown exemplarily in FIG. 11), for example a material that remains elastic during operation of handle, or be equipped with a sealing lip or ledge, flexible sealing washer, insulation film, seal ring, bellows, washer, insulating flexible foam, silicon. Sealant 19 should be such that a motion between inner and outer cylindrical elements 17.1, 17.2 and 25.1, 25.2 is still possible upon manual operation. While the elements of handle 300 described herein have a circular cross-section, for example holding element 10, outer elements 17.1 and 17.2, inner elements 25.1, 25.2, these elements can have a different cross-sectional shape, for example oval, hexagonal, square, rectangular, or other shapes. Also, inner walls 25.1 and 25.2 are made to resist bending or flexing to protect the interconnection element 30 from shocks or strong forces, for example up to 1000N. They also provide for a mechanical reference relative to rotational arm (RA) or other movable element of radiation apparatus 100, when a distance measurement sensor is used for first measurement device 50.

The circular or oval cross-section of outer cylindrical elements 17.1 and 17.2 provide for a very solid outer shell of handle, and the overlap with the inner protective walls 25.1 and 25.2, respectively can provide for mechanical and electromagnetic protection of the measurement units 40.1, 40.2, and interconnection element 30 formed by two rods 32, 34. In this respect, an interior of handle 300 at a place of measurement is protected for impact forces and shocks. Together with a seal 19, the structure provided by inner and outer elements 17.1, 17.2, 25.1, and 25.2 can also protect from dust, particles, humidity, and water. Also, holding element 10 can be made to flush and continuous with the cylindrical or oval surface of outer cylindrical elements 17.1 and 17.2, thereby providing for a smooth holding surface for an operator or user. In addition, the handle 300 is thereby made shock resistant and durable. Rods 32, 34 need to be sufficient solid to avoid breaking when a manual force or torque is applied thereto, for example preferably forces up to 100 N, but also been to bend and provide for a measurable mechanical movement to rods 32, 34 relative to inner walls 25.1, 25.2. A typical force applied by user for the movement could be in a range between 5 N and 50 N.

Moreover, an interconnection element 30 is provided that allows to interconnect the holding element 10 and base element 20, in the variant shown the interconnecting element 30 is formed by two rods 32, 34 having an upper fixation device 33, 35 to attach to holding element 10, and a lower fixation device 36, 38 to attach to base element 20. Upper fixation devices 33, 35 includes disk having a through-hole allowing for a screwable or bolted attachment to holding element 10 via a transversal cylinder. Lower fixation devices 36, 38 form a plate that is attached to square shaped-base 26, 28 of the respective base element 22, 24, for example with screws, welding, soldering, riveting, gluing with adhesives, snap-lock clips, or other type of fixed or removable attachment.

Interconnection element 30 is designed such that it is strong enough not to break or tear upon engagement of user with holding element 10, and thereby transfers torque or force or both that the user applies to holding element 10 to base element 20, and at the same time interconnection element 30 is also configured such that at least a portion of the interconnection element 30 can bend or displace upon engagement of the user with the holding element 10, when moving the main rotational arm RA. This mechanical bending or displacement of interconnection element 30 can be measured by first measurement device 50 to thereby acquire a first signal FS1 that is representative of the force or torque that is applied to holding element 10 in an effort to move the motorized arm.

In a variant, in addition to measurement a force applied to handle, measurement unit 40 can further include a sensor to measure torque applied to handle, as a third measurement device 80, in the variant shown a torque that is applied around a rotational axis expressed by the Y-direction. Such embodiment is shown in FIG. 11, where an exemplary handle 400 is shown, having a first measurement sensor 50 including two (2) distance sensors 52.1 and 52.2 that can be measure an extent of the bending caused to interconnection element 32 by a manual operation of user in two (2) different, perpendicular directions, for example in an x-direction and a z-direction, an orientation sensor 60, and a third measurement device including a torque measurement sensor 80 that is configured to measure a torque that is applied to handle 400. For example, at rod that forms interconnection element 32, a sensor that can measure a torsional strain on interconnection element 32 can be attached thereto, for example by the use of a torsion strain gage that is attached to interconnection elements 32 or other types of torsion sensors that are attached to interconnection elements 32, 34. Also, in a variant, instead of using distance measurement sensors 52.1 and 52.2, a bending measurement sensor could be used, for example strain gage sensors that are attached to a sidewall of interconnection element 30. Signals of all three sensor devices 50, 60, and 80 can be provided to data processor 70, to determine a force or torque that can be provided by one or motors MOT0 to MOT5, for providing assistive force or torque.

In another variant, handle 300 can also be equipped with a torque measurement device. For example, this can be done by equipping each rod 32, 34 of interconnection member 30 with two (2) bending, strain or other type of force measurement sensors, that can measure, for each rod 32, 34 a force that is applied in two different perpendicular directions, for example the x- and z-direction. Signals from these force measurement sensor can thereafter processed by data processor to determine a torque applied to handle 300. For example, with reference to FIG. 10, each rod 32, 34 can be equipped with a force measurement sensor that measures a force in the z-direction, for example sensor 50.2 and 50.3 (not shown). Upon applying a rotation to handle 300 in a rotative direction around the y-axis or direction, different forces will be measured in the z-direction with sensor, as compared to an application of a force in the z-direction, and this differential value between the two force measurement sensors 50.2 and 50.3 can be used as value that is indicative of a first torque around the y-axis, indication that user wants to apply a torque or turn handle 300. This value cab be used by processor 80 to determine an assistive force for any of the motors MOT1 to MOT5 to provide for torque assistance to arms RA, A1, A2, AA1, AA2, respectively.

According to another aspect of the invention, a rotation of the different movable elements RA, A1, A2, AA1, AA2, ID, XS, around the different rotational axes P1, P2, P3, P2.2., P3.2, and the linear motion of rotational arm RA along axis AM0 can be actively blocked by a braking system, for example but not limited to one or more electro-mechanical braking devices, one or more hydraulic-activated breaking devices, magnetic brakes, disk-type brakes, a drum-type brakes, or a combination thereof. These can be used for both the fully manually-moved radiation apparatus 100, or the radiation apparatus 100 that includes the motors for motor-assisted actuation, as shown in FIG. 9A. For example, a breaking device BD0 can be configured to block a linear movement of rotational arm RA along axis AM0 as a vertical brake, for example by a breaking caliper or clamp that acts on a rail of linear guiding system GRL, a braking device BD1 can be configured to block a rotation of rotational arm RA around pivot point P1, for example by acting as a electro-magnetic caliper, clamp, or a blocking bolt on an element of gearing GE1, and a breaking device BD2 could be configured to block any of the remaining rotations around pivot points P2, P3, P2.2, P3.2, for example in a drum- or disk-brake configuration, as these can be all mechanically coupled together as shown in FIGS. 6A, 6B. In that case, only one brake may be needed. However, it is also possible that the breaking system includes additional braking devices, for example for redundancy purposes and for improved safety. For example, if no mechanical coupling between arms A1, AA1, A2, AA2 exist as shown with the embodiment of FIG. 9A, for example with linking mechanism LM and arms LA1, LA2 that are represented in FIG. 6A, four (4) pivot axes P2, P3, P2.2 and P3.2 could be equipped with a braking device BD2, BD3, BD4, BD5, for safety and stabilization purposes.

Braking devices BD can be electronically controlled by a data processing unit or microprocessor, for example data processor 70 of radiation apparatus 100. For example, user or operator could press or otherwise actuate a button BUT0 or other type of user input device to unlock a vertical movement of main rotational arm RA versus support column SC, for example a button BUT0 that is placed on handle 300 and is in operative connection with data processor 70. Thereby, data processor 70 can control operation of the braking devices BD, as well as the operation of the motors MOT. For example, in a default or inactivated state, all the brakes BD0 to BD5 can be closed or activated, thereby blocking any rotation pivot axes P1 to P3.2, and the vertical linear motion of main rotational arm RA along support column SC. For safety reasons, the brakes BD0 to BD5 can also be configured to be closed when the power is cut or deactivated. Upon pressing or activating a button BUT0, or other type of user input device, user U indicates that motion to radiation apparatus 100 is intended, for example the vertical linear motion to radiation arm RA versus support column SC, this can deactivate or release braking device BD0. Upon verification that braking device BD is released, motor MOT0 can be activated or turned on to provide for motor assistance to vertical movement to arm RA. Analogously, user or operator could press or otherwise actuate a button or other type of user input device BUT2 to unblock or release a rotational movement of main rotational arm RA versus support column SC around pivot P1, and thereafter, motor MOT 1 can be activated for motor-assisted rotation, for example by activating a button BUT1 arranged on handle 300 in operative connection with data processor 70. Thereby, data processor 70 can deactivate or release brake BD1 to unblock the rotation, and at the same time can activate or otherwise turn on motor MOT1. Moreover, user or operator could press or otherwise actuate a button or other type of user input device BUT2 to unblock or release a rotational movement of arms A1, A2, relative to main arm RA, for example a button BUT2 on handle 300 in operative connection with data processor 70. Thereby, data processor 70 can deactivate or release brake BD2 to unblock the rotation, and at the same time can activate or otherwise turn on motor MOT2. Also, one button or other type of input device could block all braking devices BD, for an emergency stop. This button would also deactivate any motor MOT. All buttons BUT0 to BUT 2 could be arranged on one handle 300, for example on an outer surface of middle section 16 of holding element 10.

Data processor 70 can perform other tasks to manage brakes BD and/or motors MOT. For example, data processor can have a feedback on a rotational speed that is applied to main rotational arm RA, for example by the use of second measurement device 60 that can be embodied as an IMU, measuring rotational or translational speeds applied to arm RA or other moveable elements of apparatus 100. Upon detection of a rotational or translational speed above a certain threshold, respective ones of braking devices BD0 to BD5 can be activated to slow down or fully stop the motion for safety and to prevent damage to radiation apparatus 100. Also, second measurement device 60, or other sensors such as but not limited to rotary encoders, can give feedback on an actual position of the different arms RA, A1, A2, AA1, AA2, and upon exceeding a certain predefined motional range, for example a relative angular motional range between arms A1 and AA1 or A2 and AA2, or a maximal range along axis AM0, the respective ones of braking devices BD0 to B5 can be activated to stop the movement.

Figure 12A:
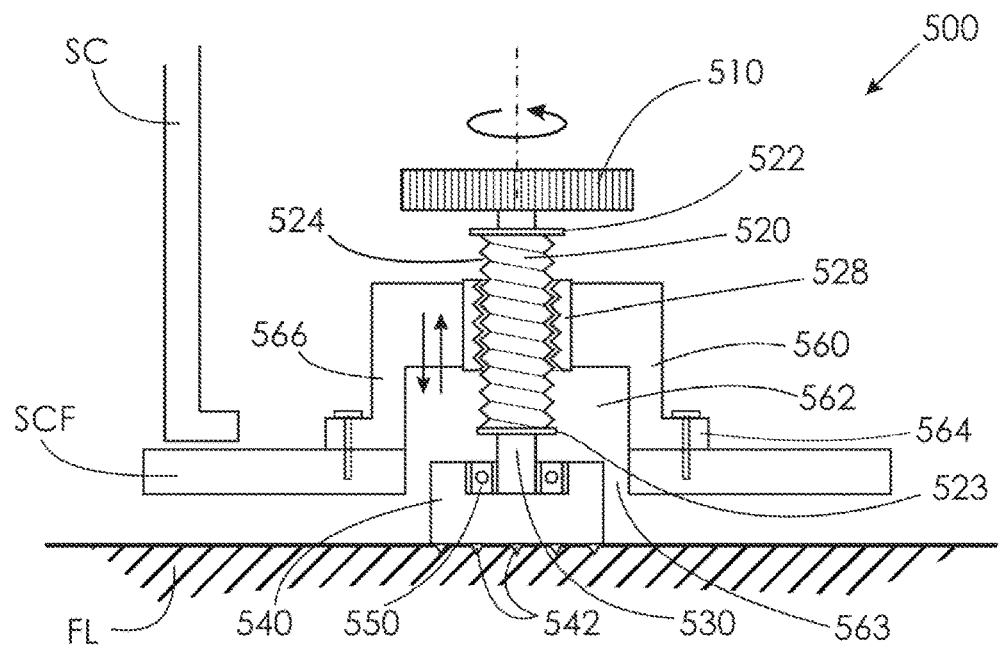
FIGS. 12A to 12C show different aspects of height-adjustable feet 500 according to an aspect of the present invention, with FIG. 12A a cross-sectional side view of an exemplary height adjustable foot 500, FIG. 12B showing another embodiment having a removable tool 570, and FIG. 12C showing a bottom view of a base BA or floor panel or board SCF of radiation apparatus 100 with a distribution of different feet 500.1 to 500.n.
Figure 12B:
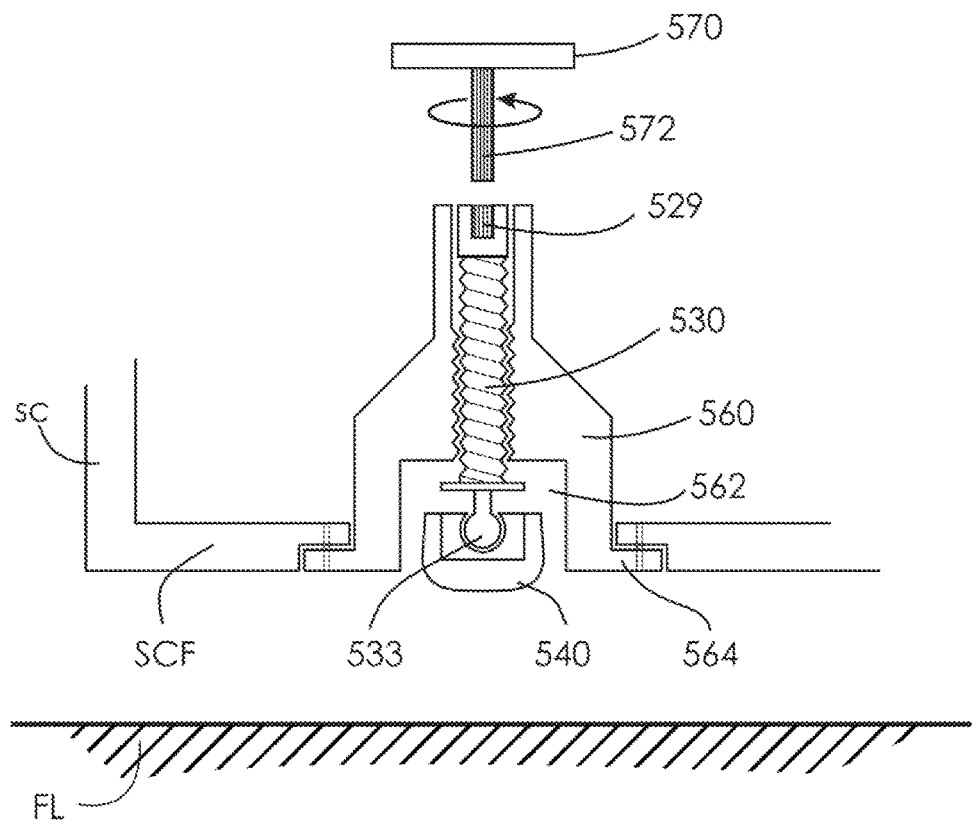
Figure 12C:
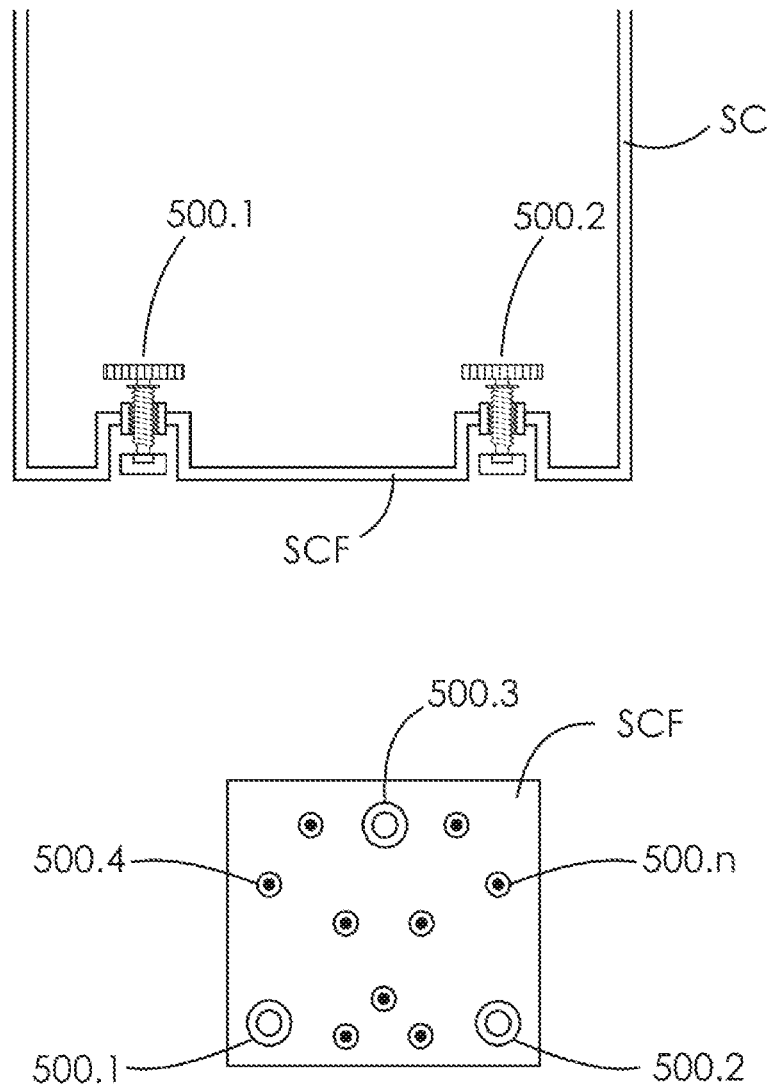

According to another aspect of the present invention, a height-adjustable auxiliary foot 500 for a stand or support column SC of a radiation apparatus 100 is provided, for example an X-ray apparatus, for stabilising the radiation apparatus 100 on uneven or bumpy grounds or floors FL, and to provide for an improved ground contact, different aspects of foot 500 shown in FIGS. 12A to 12C. When installing or otherwise placing a radiation apparatus 100 to a location of use, for example in different types of hospital or health care center environments, quite often radiation devices and apparatuses 100 are fixedly installed, either to a wall or a floor. However, quite often in case of a floor-mounted radiation apparatus 100, floor or ground FL where the radiation apparatus is to be placed is uneven, bumpy, or rough. In addition, for example when installed in field hospitals or sites in developing nations, X-ray apparatuses and other types of medical imaging apparatuses can be placed on untreated raw concrete grounds or floors, or tile flooring having uneven surface properties. This can lead to an unbalance or unstable position, and off-axis arrangement relative to a vertical axis of support column SC. Even if support column SC is bolted to a floor surface, these problems can persist. Therefore, a practical solution of floor installation and ground contact for a radiation apparatus 100 is strongly desired.

According to one aspect, a plurality of height-adjustable feet 500 are provided, preferably capable of adjustably protruding from a bottom surface or base of the support column SC, facing the floor or ground on which the radiation apparatus will be placed on. FIG. 12A shows a cross-sectional side view of an exemplary height adjustable foot 500 for a radiation apparatus 100, having a handle 510, in the variant shown a rotation knob, that is affixed, integrally formed, or in operative connection with a transversal bolt 530, transversal bolt 530 equipped with an external threading 524 that is complementary and can threadably engage with an interior threading 528 of a holding element 560 arranged at a traversing through-hole of holding element 560. A distal end of transversal bolt 530 is rotatably attached to a foot unit 540 with a ball bearing or washer 550, for example a cylindrically-shaped element made of an elastic material, for example a hard plastic. However, foot unit 540 can also be made of a hard non-elastic material, for example but not limited to a metal or an alloy. Also, it is possible that foot unit 540 and transversal bolt 530 are made from one piece of material, for example metal or a metal alloy.

Moreover, foot unit 540 can also be made to resist lateral movement when placed on to a floor or ground FL, for example protrusions 542, ribs, grooves, or other elements. Holding element 560 can include several side walls and an upper wall, forming a cavity 562 for accommodating the foot unit 540. Holding element 560 can be an integral part of floor element SCF or base BA of support column SC, or can be a separate element that is affixed to floor element SCF or base BA at an opening 563, for example by the use of bolts, rivets, screws, clips 564, or other type of attachment, for example by brazing, welding, soldering, adhesive. As radiation apparatus 10 can be relatively, for example up to one ton, holding element 560 need to be relatively solid, and can be machined from one piece of material to avoid distortion and breaking. Also, transversal bolt 530 can be made relatively solid, for example having the dimensions of M8-type or M10-type threading, or wider types of threadings.

By threadable rotative engagement of outer threading 524 with inner threading 528 of holding element 560, a manual rotation of handle 510 will cause foot unit 540 and transversal bolt 530 move upwards and downwards relative to support column SC, and therefore relative to the bottom or floor element SCF or base BA of support column SC. In a retracted position, that can be achieved by rotation of handle 510 in one rotational direction, foot unit 540 can be fully located inside cavity 562 of holding element 560 that accommodates foot unit 540, such that a lower surface of foot unit 540 is located at a higher position than a lower surface of floor element SCF or base BA. By allowing foot unit 540 to be fully retractable, it is possible to first place radiation apparatus 100 at a desired location, without that different feet unit 540 will obstruct the placement of apparatus 100, for example when apparatus 100 needs to be horizontally displaced. Thereby, lower surface of floor element SCF or base BA can be at least partially in contact with floor FL. This rotation can be limited by a ring, ledge, bolt 524 for abutting against an upper wall of holding element 560 or a part of threading 528, forming a device that can block the rotation of transversal bolt 530 relative to holding element 560. In an extended position, that can be achieved by a rotation to handle 510 in the other rotational direction, foot unit 540 can protrude or can be fully located outside lower surface of floor element SCF or base BA, to engage with an upper surface of floor FL.

FIG. 12B shows another embodiment of an exemplary height-adjustable foot 500 for a radiation apparatus 100, also as a cross-sectional side view. In this variant, transversal bolt 530 is equipped with a torque coupling device 529, for example a hex socket, torx socket, Philips socket, or other type of torque engagement mechanism for an external removable tool 570. Holding element 560 has an opening at an upper area that allows for the engagement of tool 570 with torque coupling device 529. Instead of handle 510, a removable tool 570 can be used that can be used by user to engage corresponding torque coupling device 572 of tool 570 with torque coupling device 529 of transversal bolt 530, for example a hex bolt, hex key with handle, or other torque application device. For example. tool 570 can also be embodied as a ratchet wrench with a corresponding socket or tool for torque coupling device 572, screw driver, or other types of tooling. It is also possible that tool 570 includes a torque measurement feature. Also, in this variant, distal tip or end of transversal bolt 530 engages with foot unit 540 with a ball joint 533. This allows foot unit 540 to be forced to different angular positions relative to an axis defined by transversal bolt 530. Also, foot unit 540 is shown to have a spherical shape, but other shapes are also possible, for example but not limited to conical shapes with an apex pointing downwards, square or rectangular shapes.

FIG. 12C shows a side view of a plurality of height-adjustable feet 500.1 to 500.n that are arranged close to each edge of support column SC, and a bottom view thereof, in a direction of extension of support column SC. There can be several different types of height-adjustable feet 500, arranged to be able to protrude from the lower surface of floor element SCF, having different dimensions and configurations. For example, there can be at least three (3) or exactly three (3) load-baring height-adjustable feet 500, for example arranged at corners of an equilateral triangle. These three feet 500.1 to 500.3 can be used for load-bearing and levelling of the support column SC, for example with the aid of a spirit level or bubble level. Moreover, there can be several other smaller feet 500.4 to 500.n, for example equally dispersed on the bottom of floor element, for additional support and anchoring. In the variant shown, load-bearing feet 500.1 to 500.3 have larger dimensions, for example having a transversal bolt 530 that has a larger diameter. It is also possible that the feet 500 are only auxiliary, and are arranged in addition to feet or other devices for placing radiation apparatus 100 that are not height adjustable, and in addition to a fixed installation using drill holes and screws or bolts for attachment. Also, according to one aspect, feet 500 are only auxiliary for stabilizing support column SC and thereby radiation apparatus 100, solely providing for secondary balancing stability. In this respect, the principle part of the weight of apparatus 100 can be carrier by base BA or floor element SCF. Thereby, a bottom surface of base BA or floor element SCF will be in contact with ground or floor FL. Thereafter, auxiliary load-bearing feet 500 are used and selectively extended to provide for a more stable connection between floor FL and apparatus 100 as a secondary support, whilst floor element SCF and base BA are still providing or the primary support and connection to the ground or floor FL. But it is also possible that auxiliary load-bearing feet 500 are in the fully retracted position and are not used, in cases where ground and floor is flat and horizontal.

While the different aspects of the invention has been disclosed with reference to certain preferred embodiments, numerous modifications, alterations, and changes to the described embodiments are possible without departing from the sphere and scope of the invention, as defined in the appended claims and their equivalents thereof. Accordingly, it is intended that the invention not be limited to the described embodiments, but that it have the full scope defined by the language of the following claims.

The invention claimed is:

1. A radiation imaging apparatus comprising:
a main rotatable arm that is configured to rotate around a first pivot relative to a device for pivotably holding the main rotatable arm;
a first arm rotatably attached to one side of the main rotatable arm to rotate about a second pivot, the first arm holding a imaging device;
a second arm rotatably attached to an other side of the main rotatable arm to rotate about a third pivot, the second arm holding a radiation source, a radiation axis of the radiation source is configured to irradiate an imaging plane of the imaging device; and
a linking means that links a rotation of the first arm to the rotation of the second arm such that a rotation of the first arm causes a rotation of the second arm and vice versa in opposite rotational directions for adjusting a source image-receptor distance,
wherein the linking means includes a linking mechanism rotatably attached to the first arm at a pivot point of the first arm and rotatably attached to the second arm at a pivot point of the second arm, the linking mechanism extending between the pivot point of the first arm and the pivot point of the second arm, the linking mechanism mechanically linking a rotation of the first arm with a rotation of the second arm for causing the opposite rotational directions for adjusting the source image-receptor distance.

2. The radiation imaging apparatus according to claim 1, wherein the linking means includes a linking mechanism having a transversal bar rotatably attached to the first arm at a pivot point and rotatably attached to the second arm to a pivot point, the transversal bar mechanically linking a rotation of the first arm with a rotation of the second arm for causing the opposite rotational directions for adjusting the source image-receptor distance.

3. The radiation imaging apparatus according to claim 1, wherein the linking means includes:
a first motor configured to rotate the first arm relative to the main rotatable arm;
a second motor configured to rotate the second arm relative to the main rotatable arm; and
a controller configured to control at least one of the first motor and the second motor to link a rotation of the first arm with a rotation of the second arm and vice versa, for causing the opposite rotational directions for adjusting the source image-receptor distance.

4. The radiation imaging apparatus according to claim 1, wherein the device for pivotably attaching the main rotatable arm includes a support column.

5. The radiation imaging apparatus according to claim 1, wherein a length of a first portion of the main rotatable arm on one side of the first pivot and a length of a second portion of the main rotatable arm on the other side of the first pivot are such that a first torque to the first portion that is substantially equal to a second torque of the second portion about the first pivot, for providing a rotational equilibrium between the first and the second portion about the first pivot.

6. The radiation imaging apparatus according to claim 2, wherein a first weight of the first arm and the imaging device and a second weight of the second arm and the radiation source is such that a first torque provided by the first weight to the first arm is compensated by a second torque provided by the second weight of the second arm, coupled via the linking mechanism, when the main rotational arm is in a vertical position.

7. The radiation imaging apparatus according to claim 2, further comprising:
a spring load mechanism having a spring that acts on the linking mechanism, the spring load mechanism configured such that the spring is tensioned when the first arm and the second arm are parallel to each other, and configured such that the spring progressively releases tension when the first arm and the second arm are rotated away from each other when increasing the source image-receptor distance.

8. The radiation imaging apparatus according to claim 7, further comprising:
a angle compensation mechanism that is fixedly coupled to a rotational axis that is formed at the first pivot, the angle compensation mechanism operatively coupled to the spring load mechanism, the angle compensation mechanism configured to progressively detention the spring of the spring load mechanism by displacing an attachment point of the spring when the main rotatable arm is manually moved from a horizontal position to a vertical position.

9. The radiation imaging apparatus according to claim 8, wherein a rotatable assembly including the main rotatable arm, the first arm and the imaging device, and the second arm and the radiation source are designed such that a center of gravity of the rotatable assembly lies at a distance away from the first pivot, such that a torque that is caused by the rotatable assembly around the first pivots acts to tension the spring of the spring load mechanism when the main rotatable arm is rotated from a vertical position to a horizontal position via the angle compensation mechanism.

10. The radiation imaging apparatus according to claim 2, further comprising:
a first parallelogram mechanism operatively connected to the first arm and the linking mechanism; and
a second parallelogram mechanism operatively connected to the second arm and the linking mechanism,
wherein the first and second parallelogram mechanisms are configured such that the radiation axis of the radiation source is arranged substantially at a fixed angle within a angular range relative to the imaging plane of the imaging device.

11. The radiation apparatus according to claim 2, wherein a first distance between the radiation axis of the radiation source from the main rotatable arm, and a second distance between an imaging axis of the imaging device and the main rotatable arm are different, the radiation apparatus further comprising:
a cam and pin mechanism for changing an angle of the radiation axis of the radiation source or the imaging axis of the imaging device relative to the main rotatable arm, the cam and pin mechanism configured such that the radiation axis of the radiation source points towards a center location of the imaging plane of the imaging device irrespective of an angle of orientation of the first and second arm relative to the main rotatable arm.

12. The radiation imaging apparatus according to claim 1, further comprising:
a first braking device configured to block a rotation of the main rotatable arm relative to the device;
a second braking device configured to block a rotation of at least one of the first arm relative to the main rotatable arm and/or the second arm relative to the main rotatable arm.

13. A handle for moving an arm of the radiation imaging apparatus of claim 1, the handle comprising:
a holding element configured to be held by a hand of a user to move the arm;
a base member configured to be attached to a movable element of the radiation apparatus;
an interconnection member interconnecting the holding element and the base member, a portion of the interconnection element configured to bend or displace upon engagement of the user with the holding element; and
a measurement unit configured to measure a value indicative of a force or a torque applied by the user to the handle and a value indicative of an orientation of the handle.

14. The handle according to claim 13, wherein the measurement unit includes:
a first measurement device configured to measure a bending or displacing of the interconnection member caused by the engagement of the user with the holding element to determine the value indicative of the force or the torque; and
a second measurement device configured to measure an absolute orientation of the handle.

15. The handle according to claim 13, further comprising:
a data processor operatively connected to the measurement unit for generating a value indicative of a force in a vertical direction, and configured to provide the value to a motor driver of a motor that is configured to move the arm upwards and downwards.

16. The handle according to claim 14, wherein the first measurement device includes a strain gage sensor, a proximity sensor, and/or distance measurement sensor.

17. The handle according to claim 14, wherein the second measurement device includes an accelerometer, a magnetometer, and/or a gyroscope.

18. The handle according to claim 14, wherein the second measurement device includes an inertial measurement unit (IMU).

19. The handle according to claim 13, wherein the base member includes two plates configured to be mounted to the arm, and the holding element is U-shaped.

20. The handle according to claim 14, wherein the interconnection member includes two rods or bars, and wherein the first measurement device is attached at least one of the two rods or bars.

21. The handle according to claim 13, wherein the base member includes a first protective wall that protrudes inside a second protective wall that forms a part of the holding element.

22. The radiation imaging apparatus according to claim 1, wherein the imaging device is configured to turn relative to the first arm within an angular range or the radiation source is configured to turn relative to the second arm within an angular range such that the radiation axis of the radiation source can lie within the imaging plane of the imaging device.

* * * * *